US006498143B1

(12) United States Patent
Beck et al.

(10) Patent No.: US 6,498,143 B1
(45) Date of Patent: *Dec. 24, 2002

(54) METHOD FOR ASSISTING IN DIFFERENTIAL DIAGNOSIS AND TREATMENT OF AUTISTIC SYNDROMES

(75) Inventors: Victoria Beck, Bedford, NH (US); Karoly Horvath, Baltimore, MD (US)

(73) Assignee: Repligen Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,512

(22) Filed: Nov. 24, 1999

Related U.S. Application Data

(63) Continuation of application No. 09/080,631, filed on May 19, 1998, now Pat. No. 6,020,310.
(60) Provisional application No. 60/047,049, filed on May 19, 1997.

(51) Int. Cl.[7] .............................................. C07K 14/00
(52) U.S. Cl. ......................... 514/12; 514/2; 424/198.1; 530/300; 530/324
(58) Field of Search .................... 530/350, 300, 530/324; 514/2, 12, 21; 424/198.1

(56) References Cited

U.S. PATENT DOCUMENTS

| | | | |
|---|---|---|---|
| 3,833,722 A | 9/1974 | Graybill et al. | 424/104 |
| 3,940,480 A | 2/1976 | Suenaga et al. | 424/177 |
| 4,462,991 A | 7/1984 | Higuchi et al. | 424/177 |
| 4,778,794 A | 10/1988 | Naruse et al. | 514/254 |
| 4,806,336 A | 2/1989 | Carlquist et al. | 435/22 |
| 4,920,122 A | 4/1990 | Naruse et al. | 514/254 |
| 4,994,467 A | 2/1991 | Zimmerman | 514/284 |
| 5,008,251 A | 4/1991 | Gruber | 514/43 |
| 5,094,837 A | 3/1992 | Bis | 424/9.34 |
| 5,225,407 A | 7/1993 | Oakley et al. | 514/215 |
| 5,380,872 A | 1/1995 | Sugg et al. | 548/495 |
| 5,527,825 A | 6/1996 | Karson et al. | 514/551 |
| 5,686,311 A | 11/1997 | Shaw | 436/86 |

FOREIGN PATENT DOCUMENTS

| | | |
|---|---|---|
| WO | WO 94/16756 | 4/1994 |
| WO | WO 96/06635 | 7/1996 |
| WO | WO 98/52593 | 11/1998 |
| WO | WO 99/10361 | 12/1999 |

OTHER PUBLICATIONS

Horvath et al., Journal of Peadiatrics, vol. 135, No. 5, pp. 559–563, Nov. 1999.*
Chez et al., Journal of Autism and Developmental Disorders, vol. 30, No. 2, pp. 87–94, Apr. 2000.*
Sandler et al., New England Journal of Medicine, vol. 341, No. 24, pp. 1801–1806, Dec. 1999.*
Fremeau et al., "Secretin: Specific Binding to Rat Brain Membranes"; *The Journal of Neuroscience*, vol. 3, No. 8, pp. 1620–1625 (1983).
Karelson et al., "Regulation of Adenylate Cyclase by Galanin, Neuropeptide Y, Secretin and Vasoactive Intestinal Polypeptide in Rat Frontal Cortex, Hippocampus and Hypothalamus"; *Neuropeptides*, vol. 28, pp. 21–28 (1995).
Copy of European Search Report date Jul. 5, 2002 (3 pages).
Cook et al., "The Serotonin System in Autism", *Current Opinion in Pediatrics*, 8:348–354, (1996).
Conn's Current Threrapy, Robert E. Pakel Editor, P. 452 W.B. Saunders Co. Philadelphia, PA.
Horvath et al., "Improved Social and Language Skills After Secretin Administration in Patients with Autistic Spectrum Disorders", . Assoc. Acad. Minority Physicians, 9(1):9–15 (1998).
Horvath et al., "Secretin Therapy—The Child Psychologist", *Journal of the Association for Academic Minority Physicians*, 9(1):9–15, (1998). Retrieved from the Internet: URL:http://www.childpsychology, com/autism/secret-in.htm.
Perry et al., "Secretin in Autism", *Journal of Child and Adolescent Psychopharmacology*, 8:247–248, (1998).
Ritvo et al., "A Medical Model of Autism:Etiology Pathology and Treatment", *Pediatric Annals*, 13(4):298–305, (1984).
Stedman's Medical Dictionary, 26th ed., Williams & Wilkins, Blatimore, MD, p. 486.
Willimann et al., "Lecithin Organogel as Matrix for Transdermal Transport of Drugs," *Journal of Pharmaceutical Sciences*, 81:871–874, (1992).
Beck, "Transdermal Secretin and Other Approach," (letter to www.healthboards.com/autism/1089.html) Secretin [Talk@Onelist.com (Dec. 30, 1998).
Rimland, Autism Research Review International, Jan. 1999 Update, Autism Research Institute (www.autism.com/ari/secretin2.html) (Jan. 1999).
Rimland, "Secretin update: Dec. 1, 1998," Autism Research Review International, Autism Research Institute (www.autism.com/ari/secretin2.html) (Dec. 1, 1998).
Rimland, "1998 Year–End Letter," Autism Research Institute (www.autism.com/ari/yearend.html) Nov. 30, 1998.
Westland, Secretin, email to newsgroup bit.listserv.autism (Aug. 24, 1996).

(List continued on next page.)

*Primary Examiner*—Karen Cochrane Carlson
(74) *Attorney, Agent, or Firm*—Fish & Richardson P.C.

(57) ABSTRACT

A novel relationship between pancreatico-biliary secretion and autistic syndrome is disclosed. This relationship enables a novel therapy for the treatment of the symptoms of autistic syndromes, comprising the administration of a therapeutically effective, preferably intravenous, dose of secretin to an individual with autistic syndrome. The relationship further enables a differential diagnosis for autistic syndrome, comprising an analysis of an individual's blood and/or intestinal tissue for the presence of secretin and comparison of the level of secretin to known norms.

41 Claims, 8 Drawing Sheets

OTHER PUBLICATIONS

Timpson, Secretin, email to newsgrop bit.listserv.autism (Aug. 24, 1996).

Conaty, Secretin email to newsgroup bit.listserv.autism (Aug. 25, 1996).

Conaty, Pancreatic Lipase deficiency, email to newsgroup bit.listserv.autism (Aug. 26, 1996).

Mayberry, secretin, email to newsgroup bit.listserv.autism (Sep. 10, 1996).

Mayberry, Canadian listmates, email to newsgroup bit.listserv.autism (Sep. 20, 1996).

Binstock, Secretin, email to newsgroup bit.listserv.autism (Sep. 26, 1996).

Mayberry, Peptide Homone, Substance P, email to newsgroup bit.listserv.autism (Oct. 16, 1996).

Mayberry, Substance p/Seratonin/Secretin, email to newsgroup bit.listserv.autism (Jan. 27, 1997).

Mayberry, Measles and Substance P, email to newsgroup bit.listserv.autism (Feb. 10, 1997).

Hays, Digestion—CCK/Acetylcholine, email to newsgroup bit.listserv.autism (Mar. 27, 1997).

Hays, Digestion—CCK/Acetylcholine email to newsgroup bit listserv autism (Mar. 27, 1997).

Westlund, Secretin, email to newsgroup bit.listserv.autism (Oct. 7, 1997).

Owens, Intestinal Hormones, email to newsgroup bit.listserv.autism (May 27, 1997).

Mayberry, Secretin Salve, email to newsgroup bit.listserv.autism (Jul. 17, 1997).

Harteveld et al., "Autism" Role of Drug Treatment and a Guide to its Use, *CNS Drugs*, 8(3):227–236, (1997).

Piven, "The Biological Basis of Autism" *curr Op. Neurobiol.*, 7:708–712, (1997).

Rapin et al., Neurobiology of Autism *Annals of Neurology*, 43:7–14, (1998).

Wikelgren, "Tracking Insulin to the Mind", *Science*, 280:517–518, (1998).

Wing, "The Autistic Spectrum", *The Lancet*, 350:1761–66, (1997).

Binstock, secretin, email to newsgroup bit.listserv.autism (Aug. 23, 1996).

Binstock, secretin, email to newsgroup bit.listserv.autism (Aug. 23,1996).

Mayberry, secretin, email to newsgroup bit.listserv.autism (Aug. 23, 1996).

Carlton, The Hypothalamus–specific peptides, email to newsgroup bit.listserv.autism (Jan. 19, 1998).

Carlton, Dr. Shaw's Book arrived TODAY!, email to newsgroup bit.listserv.autism (Jan. 20, 1998).

Carlton, About Dr. Shaw's Book–Careful Venting Post!, email to newsgroup bit.listserv.autism (Jan. 21, 1998).

Carlton, Secretin "gushing," email to newsgroup bit.listserv.autism (Jan. 22, 1998).

MJW28@aol.com (MJW28), Secretin, email to newsgroup bit.list.

* cited by examiner

— Pre-Tx
---- Post-Tx

METHOD FOR ASSISTING IN DIFFERENTIAL DIAGNOSIS AND TREATMENT OF AUTISTIC SYNDROMES

CROSS REFERENCE TO A RELATED APPLICATION

This application is a continuation of SN 09/080,631, filed May 19,1998, now U.S. Pat. No. 6,020,310, which claims the benefit of U.S. Provisional Application No. 60/047,049, filed May 19, 1997, the contents of which are incorporated herein.

FIELD OF THE INVENTION

The present invention relates in general to differential diagnosis and therapeutic treatment of autistic syndromes, and in particular to a new and useful method for diagnosing and treating autistic syndromes by measurement and administration of secretin.

BACKGROUND OF THE INVENTION

Autistic syndrome (or autism) is a pervasive developmental behavioral disorder of very early onset that is characterized by a fundamental lack of normal interest in other people. (Original description, Kanner L. Autistic disturbances of affective contact. *Nervous Child* 1943;2:217–250.) The recent diagnostic criteria (DSM IV) for autistic disorder are shown in Table 3 below from the American Psychiatric Association[1]

Epidemiologic studies suggested a prevalence rate of autistic behavior of approximately 2 to 5 cases in 10,000, however, recent surveys including the entire spectrum of the disease indicate that rates of 15 per 10,000 are a more accurate disease prevalence[2,3]. Such figures indicate that this disorder affects four hundred thousand Americans, with significant social and public health costs.

Despite the substantial body of evidence implicating neurobiological factors in the pathogenesis, precise etiologic mechanisms of autism have yet to be identified. In the absence of a clear etiology, although both behavioral and medical interventions are available to improve learning and behavior, there is no evidence of a cure for autism, nor any efficient psychopharmacological treatments for the core symptoms.

Autism is a syndrome with multiple etiologies, as is made clear both by the evidence of neurobiological research and by the catalog of disorders that are present with autistic behaviors[4]. Based on clinical observations, there are subgroups and subtypes of subjects with significantly different patterns of strengths and deficits, different patterns of comorbidity, levels of severity, and different psychological/cognitive profiles. The response to therapeutic trials also showed a wide variety of outcomes, which may support the possibility that there are multiple etiologies for autism. Although we know that genetic, infectious, metabolic, immunologic, neurophysiological, and environmental causes may lead to similar patterns of altered development with autistic behavior, the recognition of these clear neuropathological disorders does not help us to understand the basic pathogenic mechanism of autism.

There is no clear biological marker of autism to allow early diagnosis or screening of this disease even though it is generally believed that early recognition and management is crucial in the prognosis. Under these circumstances, every clinical observation is important and may lead us to a better understanding of this disorder.

While the specific neuropathological mechanism that produces autism is unknown, it is thought to be the result of a dysfunction of particular groups of neurons in the central nervous system. The primary structures implicated in the autistic disorder are the cerebellum, cerebral cortex, and medial temporal structures. One study showed a significant loss of Purkinje cells, and to lesser extent, of granular cells in the cerebellar hemispheres of six autistic subjects[5]. Studies of two patients with autism showed that the hippocampal pyramidal neurons in the CA1 and CA4 fields displayed a decrease in dendritic branching[6]. Metabolic dysfunction of cortical areas was found through measurements by Single Photon Emission Computed Tomography (SPECT)[7]. In addition, involvement of the medial temporal lobe has been implicated by autopsy studies demonstrating increased cell density, and small cell size in the hippocampus, amygdala, enthorhinal cortex and septal nuclei[8]. An additional argument for the temporal lobe involvement is the case report describing a child with a left lateral oligodendroglioma, who fulfilled the criteria of autistic behavior[9]. This case supports the hypothesis that damage to mesial-temporal structures at an early developmental period may lead to the autistic syndrome. Experimental evidence also supports this argument. A two-stage removal of the amygdalo-hippocampal complex in newborn monkeys resulted in behavioral changes (abnormalities of social interactions, absence of facial and body expressions and stereotypical behavior), resembling autism in children[10]. It is important to note that subgroups of autistic children displayed distinct patterns of brain activity in the frontal and temporal regions. Differences were more prominent in the left than the right hemisphere[11]. Four adult patients with autism had regionally decreased blood flow in the right lateral temporal, and in the right, left, and midfrontal lobes compared with controls[2].

The neurobiological etiology of autism is supported by the observation that epilepsy is a common concomitant of autism[13], affecting approximately one-third of adults who had childhood autism which usually had began in infancy or adolescence. In addition, different subgroups of patients have exhibited a variety of biochemical/immunological abnormalities. For example, in 20–40% of patients, whole blood serotonin levels are elevated[14], and platelet serotonin is altered. Other observations include changes in the levels of dopamine-beta-hydroxylase (DBH) in plasma[15], elevations in the levels of beta-endorphin, norepinephrine, arginine-vasopressin, and abnormally low levels of adrenocorticotropic hormone in 70% of autistic children[16], however, there are no supporting data for the autoimmune mechanism and the therapeutic trials with steroid treatment are disappointing so far.

Drug trials for autism have included tests of the effects of dopamine agonists, and antagonists to dopamine, serotonin and opiates, as well as beta blockers, ACTH analogs, and oxytocin[18]. Most of these treatments were associated with some beneficial effect in small groups of patients. The broad range of biochemical abnormalities that stimulated this wide diversity of pharmacotherapeutic trials is a clear indication that we are still far from the understanding the main pathological events in the brain resulting in autistic behavior.

Two recent hypotheses of autism are the opioid- and the immune theory. The opioid theory is based on the observation that the main features of autism are similar to features of opiate addiction. The autistic-like behavior elicited by opiate administration include: reduced socialization, affective lability, repetitive stereotyped behavior, episodes of increased motor activity, diminished crying, insensitivity to pain, and poor clinging. Motivated by this similarity, clinical trials have been conducted by using an opioid antagonist, naltrexone, in autistic patients. In an open trial, 8 to 10 children were judged to show a positive response to naltrexone[19]. However, more recent double-blinded studies found that naltrexone treatment failed to produce significant changes in social behavior[20].

Other researchers suppose that the opioids are derived from food sources. The enzymatic digest of casein and gluten contains peptides with opioid activity[21]. Fukudome and Yoshikawa isolated four opioid peptides from the digest of wheat gluten[22]. One of these peptides occurred in 15 different sites in the primary structure of glutenin, which is high molecular weight protein in wheat and considered as innocent protein in celiac disease. An additional indirect argument for the possible role of exogenous peptides was the presence of an abnormal urinary peptide pattern in patients with autism[23]. Although there is no scientific evidence that these exogenous peptides may enter the bloodstream, open clinical trials in Norway have been undertaken with the long-term elimination of gluten and casein from the diet of patients with autistic behavior and found only mild improvement[24]. As can be seen by prior research studies, while administration of opioids causes autistic behavior trials with specific and very restricted diets and opioid antagonists have not resulted in evident improvement in the behavior and health of autistic patients.

Certain immune-system abnormalities have been observed in connection with autism, such as cell-mediated immune response to human myelin basic protein[17] and changes in the percentage of different subpopulations of lymphocytes[25]. The followers of immunopathogenesis theory are trying to use large doses of steroids. The administration of steroids resulted in some improvement in the behavior of few patients. However, to maintain this improvement, continuous administration of large doses of steroid were necessary, accompanied by all the side effect of chronic steroid administration. A tapering of the therapeutic dosage of steroid resulted in an immediate relapse.

A significant portion of patients with autistic behavior also suffer from mild gastrointestinal symptoms, such as abdominal distension, constipation, or chronic loose stools. Although these gastrointestinal problems are well known, they are not considered as important clinical features of the autistic syndromes, nor have they been treated except symptomatically. Autistic children with chronic diarrhea are not referred routinely to a pediatric castroenterologist. In a recent study, 43% of patients had altered intestinal permeability[26], which is a strong argument for an intestinal dysfunction in a significant portion of autistic patients.

Secretin is a 27-amino acid peptide hormone produced by the S-dells of the small intestine that are spatially distributed from the upper crypt to the villus tip, being particularly numerous in the upper two-thirds of the villi[27]. The release of secretin is increased by the products of protein digestion, acid bathing, fat, sodium-oleate, bile and herbal extracts[28] (see FIG. 1A). Secretin increases the secretion of bicarbonate in the pancreas and biliary tract, resulting in secretion of a watery, alkaline pancreatic fluid (see FIG. 1B). The effect of secretin on the pancreas and bile duct is mediated primarily by secretin-induced elevation of cyclic AMP[29], and does not involve the inositol phosphates signal transduction pathway (see FIG. 1C).

Secretin regulates the growth and development (enzyme composition) of the stomach, small intestine, and pancreas, and stimulates pancreatic fluid secretion, and bile secretion[31]. In addition, secretin has secretory, motility and circulatory effects in the gastrointestinal tract. Secretin stimulates immunoglobulin excretion through bile[32]. Secretin increases superior mesenteric blood flow, and its distribution within the mucosa and submucosa[33], as well as lymph flow[34] (see Table 1).

Thus far, the clinical uses of secretin are based on its secretory and vascular effects. The two most important diagnostic applications are the examination of pancreatic function, and the diagnosis of gastrinoma. There is no accepted therapeutic use. A trial to use secretin in intrahepatic cholestasis in small numbers of patients initially was encouraging[35], however, a double-blind placebo-controlled multicentric trial found no statistically significant differences in the reduction of serum bilirubin levels between secretin and placebo groups[36].

The structure of porcine secretin has been known for some time and it has been isolated from porcine intestine, and has been found to be constituted by a peptide composed of 27 armino acid residues[37]. Moreover, it has been found that bovine and porcine secretins are identical but that they are markedly different from chicken secretin[38]. Although bovine and porcine secretins behave identically with human secretin in some respects they are not structurally identical (4,806,336 Carlquist et al. 2/89). U. S. Pat. No. 4,806,336 (Carlquist et al.) discloses the chemical composition of human secretin, a method for administering secretin for diagnostic use in determining pancreatic or gallbladder function, and a method for stimulating pancreatic secretion in man.

There is no published information suggesting a direct relationship between autism and secretin. However, it has been proposed that secretin and receptors of secretin are present in the brain areas that are thought to be involved in autism. Although exactly how secretin works in the brain is not yet fully understood, it seems likely that secretin regulates neurotransmitters and influences the function of a variety of cells, especially in the "hippocampal" and "amygdaloid" brain areas, where seem to be impaired in autism. (See Table 2.)

Our observations described in detail herein suggest that secretin is effective in the treatment of both gastrointestinal and behavioral/developmental problems in some children with autism. We observed that a group of young autistic children with chronic diarrhea, while they were undergoing, tests involving an injection of secretin, had an extraordinary increase in the production of fluid from their pancreas. During the follow-up clinical visits these same children showed impressive progress in their social, behavioral and language skills, which appears so far to be permanent. We also found that the children who showed these responses to injected secretin produced only small amounts of their own secretin, and when given a dose of secretin by injection, they were able to produce an elevation in the blood level of another hormone, serotonin, which has effects on the brain.

These observations demonstrate the close relationship between secretin and serotonin in a group of autistic children. Our findings suggest that there are two subgroups of autistic patients, distinguished on the basis of gastrointestinal symptoms, their own blood secretin levels, the increase in serotonin level after secretin injection and the quantity and quality of fluid produced for secretin stimulation. In addition, we found high prevalence of other gastrointestinal abnormalities (inflammation in the esophagus, digestive enzyme deficiencies) in children with autistic behavior which adds further support to a relationship between the presence of gastrointestinal dysfunctions and autism.

Thus, we have discovered that the gastrointestinal/brain hormone secretin has a beneficial therapeutic effect on the gastrointestinal and brain function in certain autistic children. Our findings are the first clear evidence for an association between brain and gastrointestinal dysfunctions in autistic children.

With no prior findings of secretin having the capability to influence human behavior, there has been no research into the effect of secretin on autistic disorder. This invention is based on the unique and dramatic clinical observations of the effect of secretin administered for the diagnostic evaluation of gastrointestinal function in children with autistic behavior. These observations included:

(1) significant improvement in the social communication (language) and behavioral skills; and (2) hypersecretion of pancreato-biliary fluid in children with autism and chronic loose stools.

These observations described here open an entirely new direction in the autism research and may help to understand the pathogenesis of this disease. In addition, it may lead to a better understanding of the role of gut peptide hormones in the brain function. The existence of the gut-brain axis has been hypothesized, however, there was no clear clinical entity associated with this axis until now. This observation is the first clear evidence for an association between Gastrointestinal and brain dysfunctions.

SUMMARY OF THE INVENTION

It is an object of the invention to provide a definitive method for the diagnosis of autism.

It is another object of the invention to provide an effective treatment for autism which does not require large doses of steroids or other medications.

It is a further object of the invention to provide an effective treatment for autism which does not require frequent dosage.

A particular advantage of the invention is the effectiveness of the treatment with a single dose of a non-steroidal hormone, and the continued effectiveness with follow-up doses.

These objects and others are accomplished by the stimulation of the pancreatico-biliary fluid secretion by the hormone, secretin, in a patient exhibiting autism. The release may follow the exogenous administration of an effective amount of the secretin hormone itself or, alternatively, may be subsequent to the exogenous administration of a substance that stimulates the release and/or production of secretin.

These and other objects, features, and advantages, which will be apparent from the following discussion, are achieved, in accordance with the invention, by providing a novel, therapeutically effective, preferably intravenous, dose of secretin, so as to alleviate the symptoms of autism in certain individuals suffering from autistic syndromes. Additionally, oral, intramuscular, intra-articular, intradermal, subcutaneous, inhalation, and rectal routes of administration are believed to be effective. Our observations indicate that the particular administration route is not critical to the invention.

As discussed in detail herein, the preferred means of stimulating the release of pancreatico-biliary secretion is by intravenous administration of a bolus of secretin in solution. However, alternate, less-invasive, routes of secretin application from external sources, such rectal and intradermal routes, are contemplated herein. As is known in the art, such administration would require attachment of certain biologically acceptable chemicals to assist in the mucosal or dermal absorption (know as permeation enhancers) and to protect against hydrolysis by the colonic bacterial flora or other cellular enzymes.

Alternate means of stimulating secretin release, other than exogenous administration of secretin itself, are also contemplated herein. Specifically, as previously discussed, certain agents when delivered orally cause the body to release secretin. For example, studies have shown that a decrease in the pH of the duodenum below 4.5 results in a significant secretin release. Administration of hydrochloric acid has been shown not only to stimulate the release of secretin but also to stimulate the biosynthesis of secretin [Murthy, *Gastroenterology* 80:1237 (1981)]. Likewise, gastric acids can trigger the release of secretin. Therefore, it is clear that exogenous administration or endogenous production of acidic agents can lead to the release of secretin as well as the endogenous production of the hormone.

Other agents linked to secretin production and/or release include but are not limited to 1-phenylpentanol or 1-phenyl-1-hydroxy-N-pentane (PHP); bile salts and acids; fats and fatty acids such as sodium oleate and oleic acid; anti-ulcer compounds such as PLAUNOTOL™, tetraprenylacetone (TPN), geranyl-geranyl acetone (GGA), and (Z)-2-(4-methylpiperazin-1yl)-1-[4-(2-phenyl-ethyl)phenyl]-ethanone oxime hydrochloride monohydrate (MCl-727); and herbal extracts such as licorice root. Thus, it is within the scope of the invention to exogenously administer a substance that can either stimulate the release of secretin or stimulate the endogenous production of the hormone.

The various features of novelty which characterize the invention are pointed out with particularity in the claims annexed to and forming a part of this disclosure. For a better under standing of the invention, its advantages and objects, reference is made to the accompanying descriptive matter in which a preferred embodiment of the invention is illustrated.

BRIEF DESCRIPTION OF THE DRAWINGS

FIG. 1A depicts the intestinal phase of pancreatic secretion. FIG. 1B depicts the generally accepted mechanism of bicarbonate secretion from the pancreatic duct cell. FIG. 1C depicts the generally accepted mechanism of protein secretion from the pancreatic acinar cell, particularly the relationship between secretin and cAMP and phosphorylation of regulatory proteins.

DETAILED DESCRIPTION OF THE INVENTION

Figure 1A:
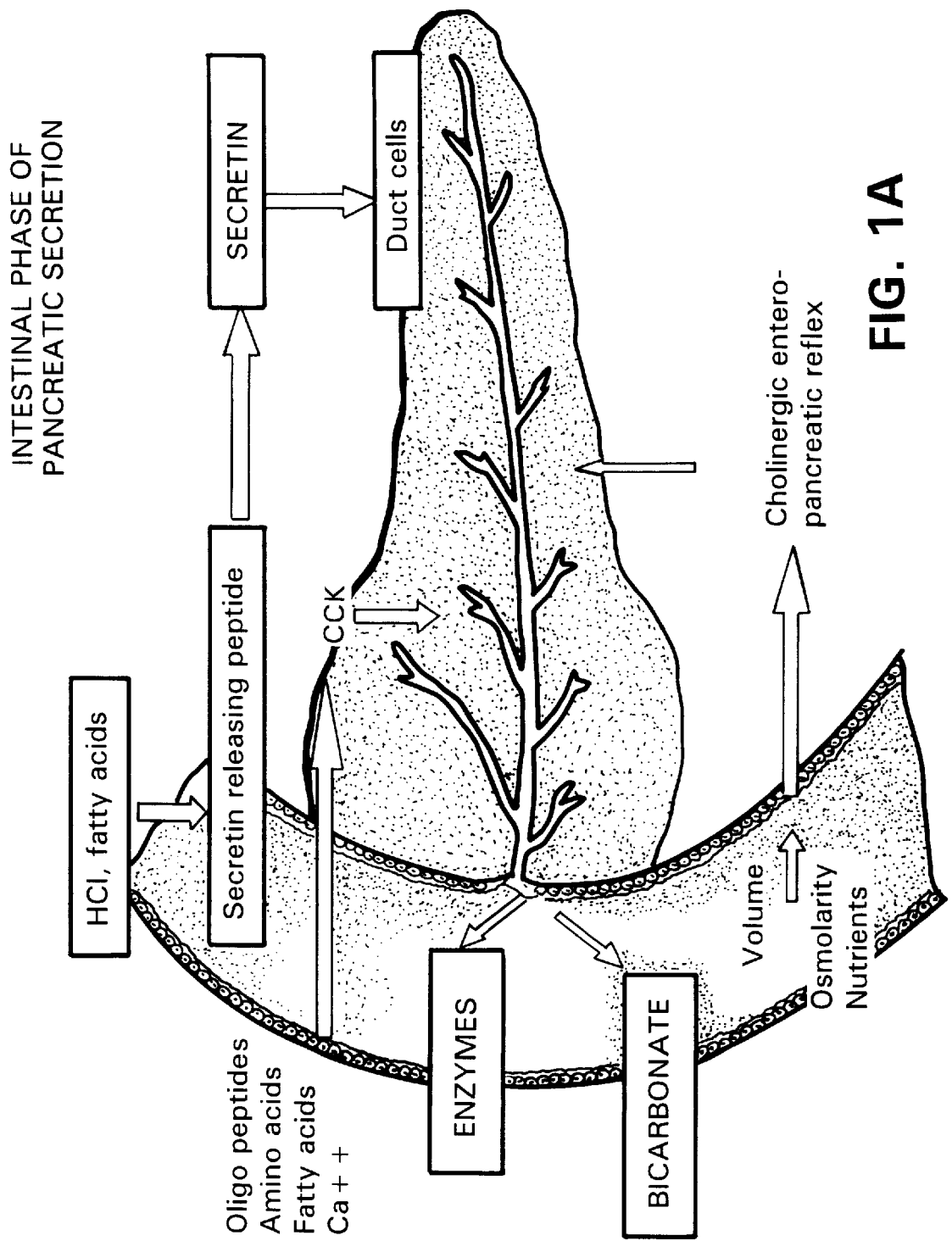
FIGS. 1A–1C: Depicts the cascade of reactions related to secretin.

With the exception of our data, there is not any other observation which links the intestinal peptide hormone, secretin, to the autistic syndrome. This is the first observation demonstrating a significant improvement in a neuropsychological disease after administration of a gut-peptide. Perhaps more importantly, these findings should provide the basis of new group studies that focus on the brain-gastrointestinal axis and its role in other neurological disorders. As far as the secretin is concerned, it was not considered as a clinically important neuropeptide in the brain, although several studies suggest that secretin may influence the function of the cells in the brain. Secretin receptors in the rat brain may be coupled to adenylate cyclase in a stimulatory manner[39]. Secretin injection was strikingly effective in increasing circadian rise of LH and FEB secretion in ovariectomized, estrogen-primed rats[40].

There are few studies demonstrating the presence and possible production of secretin in the brain. Secretin-like immunoreactivity (SLI) has been identified and characterized in the pituitary, hypothalamus, pineal and septum[41,42]. The relatively high concentration of secretin in the hypothalamus raises the possibility of a secretinergic pathway between the brain and the neurointermediate lobe of the pituitary[42]. The concentration in the neurointermediate lobe is about 45 fold higher than the concentration of SLI observed in the anterior lobe[42].

The existence of a possible brain-gut relation is supported by the fact that the nucleotide sequences of the coding regions of the secretin precursor RNAs (and thus the precursor proteins) produced in the small intestine are identical to those in brain and hypophysis[43]. Thus, although the role of secretin in the function of CNS has not yet been fully elucidated, it seems likely that secretin participates in neurotransmitter regulation, and influences the function of different cells (Table 1). Considerable data suggest that these effects are mediated via cAMP in hypothalamus and hippocampus[39].

TABLE 1

Physiologic Effects Of Secretin

| GASTROINTESTINAL TRACT | CENTRAL NERVOUS SYSTEM |
|---|---|
| Secretory effects (stimulatory--pancreas, biliary tract) | Adenylate cyclase activation (cAMP) |
| Trophic effect (intestine, pancreas, stomach) | Tyrosine hydroxylase activity (increase) |
| Circulatory effect (selective -- intestine, pancreas) | Dopamine metabolism |
| Motility effect (inhibitory -- stomach, intestine) | Prolactin secretion (increase) |

Regional distribution studies indicated that the specific receptor binding of secretin was greatest in the cerebellum, intermediate in the cortex, thalamus, striatum, hippocampus, and hypothalamus, and lowest in the midbrain and medulla/pons[44]. Interestingly, secretin binding was found in the regions of the brain where abnormalities were found in autism (Table 2).

TABLE 2

Localization of Secretin vs brain areas with proposed dysfunction in autism.

| | | Secretin* | | | | |
|---|---|---|---|---|---|---|
| Brain area or cells | Autism | Binds to receptors | +SLI found | Precursor gene found | Activates adenylate cyclase | Binds to VPI receptors |
| Cerebellum | Yes | Yes | | | | |
| Cortex | Yes | Yes | | | | Yes |
| Hippocampus | Yes | Yes | | Yes | Yes | Yes |
| Amygdaloid | Yes | | | | | |
| Hypothalamus | | Yes | Yes | | Yes | |
| Medulla/pons | | | | Yes | | |
| Hypophysis | ? | | Yes | Yes | | |
| Thalamus | | Yes | Yes | Yes | | |
| Striatum | | Yes | | | | |
| Glioblasts | | | | | Yes | |

[+SLI - Secretin-like immunoreactivity. *Not all area was examined]

Specific receptors for secretin have been characterized. Northern blot analysis of human tissue mRNA revealed that the relative intensity for expression of a 2.1-kilobase HSR transcript was pancreas>kidney>small intestine>lung>liver, with trace levels in brain, heart, and ovary. The human secretin receptor showed a homology of 80% with the rat secretin receptor and 37% with the human type 1 vasoactive intestinal peptide receptor[45].

There are several possible explanations for the CNS effect of secretin in patients with autistic spectrum disorders:
(a) secretin receptors are present in brain areas with proposed dysfunction in autism (so far, no one has examined this possibility);
(b) secretin increases the cAMP concentration in the glioblasts[46], hypothalamus[47], paraventricular nuclei, supraoptic nucleus[48], and hippocampus (alterations in the hippo-campal formation are strongly suspected in autism[49]);
(c) secretin may act by activating the VIP-1 receptors, which are predominately found in the cerebral cortex and hippocampus[50].
(d) secretin may have the same circulatory effect in the brain as in the gut, and may increase the cerebral blood flow in the area of brain containing secretin receptors such as hypothalamus, hippocampus and cortex (the comparison of pre- and post secretin SPECT studies in Case 1 showed a marked improvement in the cerebral blood flow after secretin administration, which perhaps supports such a mechanism);
(e) the hydroxylation of tyrosine to dopa is the rate-limiting reaction in catecholamine biosynthesis (it has been previously reported that secretin and other members of the secretin-glucagon family of peptides increase dopa synthesis in superior cervical ganglia in vitro[51]; it is possible that secretin influences brain catecholamine metabolism through activation of tyrosine hydroxylase); or
(f) there is a possibility of imbalance between secretin and antagonist neuropeptide hormones in the brain (for example, an imbalance between secretin and somatostatin, secretin and Peptide YY, and/or secretin and glucagon, may result in an increased or decreased sensitivity to another substance).

Secretin injected intracerebroventricularly (ICV) significantly increased defecation and decreased novel-object approaches in rats, but showed no significant effects on stereotypic behavior[52]. No autistic rat model exists in which it could be determined whether secretin relieves autistic symptoms in rats. There is no report of secretin influencing human behavior. A relation-ship between secretin and human behavior has never been shown or proven.

The examples contained herein are provided for illustrative purposes only, and are in no way intended to limit the scope of the present invention.

Materials and Methods

Patients

Children with autistic behavior were recruited from the Pediatric Gastroenterology and Behavioral and Developmental Pediatric Clinics at the University of Maryland. In each case, the diagnosis of autism was based on the DSM-IV criteria set forth below (Table 3) and was confirmed by pediatric neurologists experienced in evaluating pervasive developmental disorders.

TABLE 3

DSM-IV Criteria for Autistic Disorder

A. A total of at least six items from (1), (2), and (3), with at least two from (1), and one each from (2) and (3).
   1. Qualitative impairment in social interaction, as manifested by at least two of the following:
      a. marked impairment in the use of multiple nonverbal behaviors, such as eye-to-eye gaze, facial expression, body postures and gestures to regulate social interaction
      b. failure to develop peer relationships appropriate to developmental level
      c. a lack of spontaneous seeking to share enjoyment, interests or achievements with other people (e.g., by lack of showing, bringing, for pointing out objects of interest)
      d. lack of social or emotional reciprocity
   2. Qualitative impairments in communication, as manifested by at least one of the following:
      a. delay in, or total lack of, the development of spoken language (not accompanied by an attempt to compensate through alternative modes of communication such as gesture or mime)
      b. in individuals with adequate speech, marked impairment in the ability to initiate or sustain a conversation with others
      c. stereotyped and repetitive use of language or idiosyncratic language
      d. lack of varied spontaneous make-believe play or social imitative play appropriate to developmental level.
   3. Restricted, repetitive, and stereotyped patterns of behavior, interests, and activities, as manifested by at least one of the following:
      a. Encompassing preoccupation with one or more stereotyped and restricted patterns of interest that is abnormal either in intensity or focus
      b. apparently inflexible adherence to specific, nonfunctional routines or rituals
      c. stereotyped and repetitive motor mannerisms (e.g., hand or finger flapping or twisting or complex whole body movements)
      d. persistent preoccupation with parts of objects
B. Delays or abnormal functioning in at least one of the following areas with onset prior to age 3 years:
   1. social interaction,
   2. language as used in social communication, or
   3. symbolic or imaginative play
C. Not better accounted for by Rett disorder or childhood disintegrative disorder.

American Psychiatric Association, Diagnostic and Statistical Manual of Mental Disorders, 4th ed. 1994.

Patients were evaluated for abnormal bowel movements, evidence of reflux esophagitis, tissue activities of digestive enzymes, volume and contents of secreted pancreaticobiliary fluid after secretin stimulations, blood levels of peptide hormones and neurotransnnitters and presence of intestinal bacterial or candida overgrowth. The specific procedures were as follows.

Upper Gastrointestinal Endoscopy and Pancreatic Stimulation

Chronic, non-infectious diarrhea with unclear etiology was the indication for upper gastrointestinal endoscopy. The full upper gastrointestinal work-up included biopsies for histology, measurement of the digestive enzymes of the small intestine (lactase, maltase, sucrase, glucoamylase) and the pancreas (amylase, lipase, trypsin, chymotrypsin).

After fasting from midnight, upper gastrointestinal endoscopies were carried out the next morning under general anesthesia. All gastric juice was aspirated before passing the endoscope into the duodenum. The pancreatico-biliary juice was collected after positioning the endoscope distal to the ampulla of Vater. An ERCP catheter was placed into the channel of endoscope and the fluid was collected by moving the tip into the outcoming fluid and suctioning it into a syringe. The pancreas was then stimulated with secretin 2 IU/kg BW (Ferring Laboratories, Inc, Suffern, N.Y., USA) given intravenously within a minute. Three additional specimens were collected after the secretin injection within a 10-minute period. Blood samples were collected prior to and 10 minutes after secretin stimulation. In a subgroup of children, the effect of duodenal acidification was determined by measurement of blood secretin levels before and 4–5 minutes after washing the second part of the duodenum with 0.05M hydrochloric acid for 5 minutes. At the end of the procedure, biopsies were obtained of the small intestine, esophagus and stomach.

Analyses

The volume of secreted fluid was calculated as ml/min and the aspirated juice analyzed for pH, protein (mg/ml; Bio-Rad protein assay), and for enzymes (amylase, trypsin, lipase, chymotrypsin, and carboxypeptidase A and B). These enzyme assays were modified by us and run regularly in our certified Clinical Laboratory. An aliquot of collected fluid was sent for bacterial and fungal culture. Intestinal biopsy specimens were homogenized in ice-cold distilled water and the activities of lactase, maltase, sucrase, palatinase and glucoamylase were measured using the Dahlquist intestinal disaccharidases assay [Dahlquist, *Anal. Biochem*, 22:99–107 (1968); Azad M, *Pediatr Res*, 1990;28:166–170 (1990)]. The normal values were established based on measurements of histological normal intestinal biopsy tissues (n=104) at the University of Maryland. In our practice, digestive enzyme activities below the established 3d percentile values are considered abnormal.

Examination of the biopsies of esophagus for reflux esophagitis used the following histological criteria: eosinophilic or lymphocytic infiltrate in the squamous epithelium, basal layer thickening and papillary hypertrophy. The gastric biopsies were stained with Giemsa to identify Helicobacter pylori infection.

Blood samples were analyzed for the levels of gastrointestinal peptide hormones (Secretin, CCK, VIP, Peptide Y) and neurotransmitters (Serotonin, Substance P). All the assays were performed in the Interscience Institute (Inglewood, Calif.) specialized in Gastrointestinal hormone measurements Behavioral Evaluation Prior to the secretin administration, each child underwent developmental/psychological evaluation. The post-secretin evaluation was based upon the notes of therapists and teachers who did not know about the treatment, and parent interviews and videotape recordings of child behaviors. In addition, most underwent a structured evaluation including assessment of intelligence, language ability, adaptive function [Vineland Adaptive Behavior Scales][53] and behavioral rating scales [Child Behavior Checklist][54]. A more specific measure directly related to autism, the Childhood Autism Rating Scale [CARS][55], was also used.

The most recent 8 cases had developmental/psychological evaluations at the University of Maryland or at the Kennedy Krieger Institute prior to the secretin administration.

Specific Case Studies

Figure 3A:
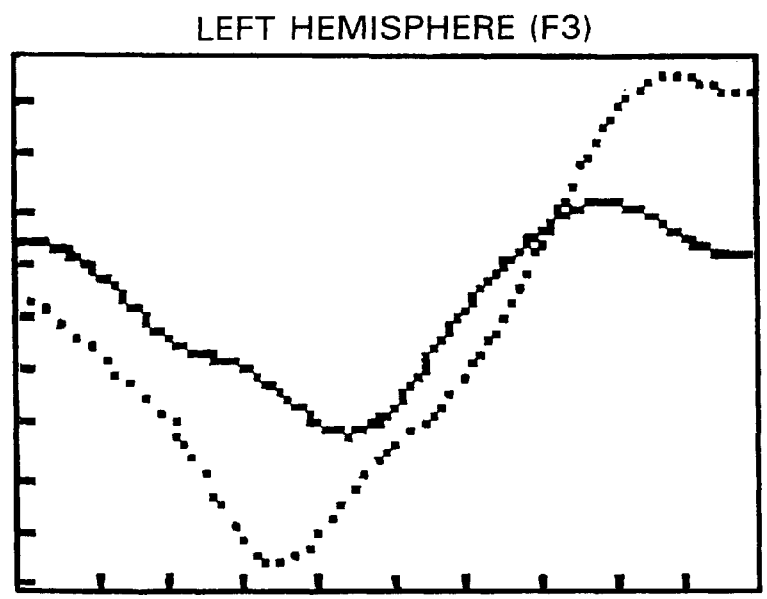
FIGS. 3A–3B: Depicts the results of an Evoked Potential Response Test on Case 1 (JB) after an injection with secretin.
Figure 3B:
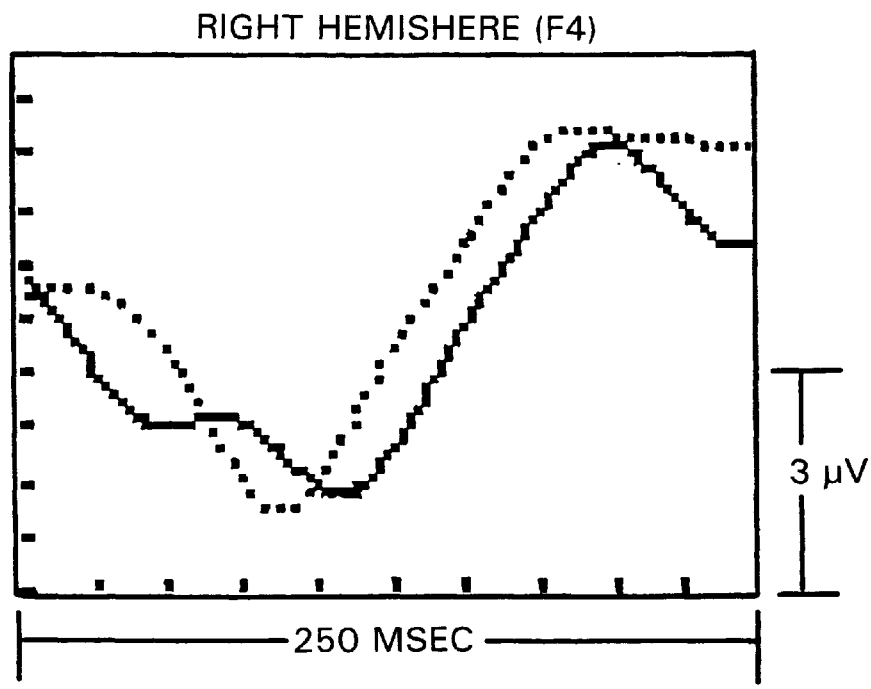

Case 1. J. B., a 3 and 3/12 year old boy, was the product of a full-term uncomplicated pregnancy. Development of language and social behavior proceeded normally until about 15 months of age. At that time he lost his expressive vocabulary and his social behavior deteriorated. He was clinically diagnosed with autism by a pediatric neurologist at 1-½ years of age. At 2-½ years of age, a multidisciplinary evaluation changed the diagnosis to PDD not otherwise specified. Brainstem evoked potential studies revealed abnormal responses to frequency modulations in sound, which suggested the involvement of the temporal lobes and the thalamocortical afferents. Single photon emission computed tomography (SPECT) scan of the brain revealed decreased perfusion in the right hemisphere, with the most severe decrease in the right parietal-temporal region. Because of his chronic diarrhea and elevated antigliadin IgG antibody titer, he underwent an upper gastrointestinal endoscopy. After the administration of 2 IU/kg BW of secretin, the patient had an extraordinary pancreatic secretory response (10 ml/mien). Three weeks after the procedure his mother reported significant changes in his gastrointestinal symptoms and behavior. His chronic diarrhea resolved and he became potty-trained. More dramatic changes occurred in his autistic behavior (Table 4). Among these were improvements in eye contact, alertness, expressive language, and fine motor skills. Eight months after the procedure he has still retained his cognitive gains. At that time, he received a second single secretin infusion which resulted in a further improvement in his language and cognitive functions. The latest behavioral evaluation indicates that he has changed from a low functioning autistic child to a social, non-autistic, speech-delayed child. Repeat evoked potential studies indicated only a minimal delay in responses eight months after secretin administration (see FIGS. 3A and 3B). In addition, there was a less marked decrease in perfusion of right posterior parietal and right temporal lobes upon follow-up SPECT imaging when compared to the previous study.

TABLE 4

Changes after Secretin Stimulation in Case #1 (age 3.5 years)

| Before Secretin | Progress after Secretin administration (within two months) |
| --- | --- |
| Two words | 100's of words - will repeat some approximation of any word requested |
| No sentences | Short sentences, such as "I love you", "I want juice", "Good night mammy" |
| No flash cards | 40–50 flash cards |
| No focus on requested tasks | Will sit and watch carefully. Will perform most tasks after watching once or twice. Will sort by color or category. Will construct more complicated puzzles. Will respond appropriately to "what's this"? |
| Diapers only | Completely potty trained |
| Watch videos | Now gets "involved" interactively with his videos. He will imitate the hand motions, sing the songs or dance to the music. |
| Consistent sleeping problems | Has slept through almost every night entirely |
| Infrequent (1–2 times/week) "spinning" episodes | No spinning episodes |
| Abnormal bowel movements | Normal bowel movements |
| Excessive water consumption | Excessive water consumption - no change |
| Limited diet preferences | No change |
| No apparent connections made between language and objects | Many connections made between new language learned and objects. Recites names he has learned on flash cards when he sees the same on computer game or video. |
| No response to request for gestures | Responds to all kinds of requests and spontaneously says these things himself. |
| No interest in drawing | Wants to draw constantly. Will draw complete face and name the parts as he draws. |
| Did not imitate commands | Will imitate almost any multi-step command |
| Minimal eye contact | Eye contact 75% of the time |

Case 2. A. S., a 5 year old boy with autism, was referred with a two year history of diarrhea and food intolerance. His prenatal and postnatal history were unremarkable. His autism was diagnosed by a pediatric neurologist at two years and 9 months of age. According to his parents, he appeared normal and responsive until about 2 years of age, when he completely lost his speech and no longer responded to his name. He was placed on a high dose steroid therapy at age 4 with mild improvement. However, the beneficial effect diminished with a relapse during the gradual steroid discontinuation. Intravenous immunoglobulin was initiated later, but did not result in sustained benefit. During the endoscopy he received 2 IU/kg body weight of secretin. There was also a significantly increased secretory response after secretin administration (7.5 ml/min). The cognitive skills of this boy improved over a five weeks period following a single dosage of secretin, and he continues to progress (Table 5). He received a second dose of secretin 3 months later, which caused a further improvement in his social behavior and language.

TABLE 5

Changes after Secretin stimulation in case #2 (age 6 yrs).

| Category | Before Secretin | Changes after Secretin | Time |
| --- | --- | --- | --- |
| Alertness, concentration | Staring into space; self-stimulation; does not pay attention | Extremely alert: looking therapist directly in the eye; responds immediately to commands | 2 days |
| Correct responses to drills | Often guessing; not paying attention; 50% correct responses | Responds more quickly; pays better attention; 75–80% correct responses | 1 week |
| Receptive language | Variable; understands 20–30% of commands; mostly one-step commands | Retrieves objects; follows 2–3 step commands; understands where he is going; understands 75% of commands | 3 weeks |

TABLE 5-continued

Changes after Secretin stimulation in case #2 (age 6 yrs).

| Category | Before Secretin | Changes after Secretin | Time |
|---|---|---|---|
| Expressive language | Rarely repeats words | Repeats 20–30% of what he hears; starting to verbalize on his own; "give me"; "come on" pointing to letters on ABC's and saying them "V", "W", "X", "Y", "Z". | 4–6 weeks |
| Sleep | Sleeps 7–8 hours; often wakes up at night | 10–12 hours per night uninterrupted every night | 1 day |
| Fine motor | Very poor fine motor coordination | Putting together Legos; turns key in door; turns small knobs | 4 weeks |
| Gross motor | Will climb steps; rides bike with assistance | Starts to hang on monkey bars; goes down fire pole with help; riding his bike up hill and into new areas | 4 weeks |
| Activity level | Hyperactive even during drills; self simulations during drills and school | Very energetic but has very good focus during drills | 1 week |
| Appetite | Variable; eats one meal per day; eats only 1–2 foods | Eating more foods; 2–3 large meals per day; increased variety of foods; wanted to eat dairy | 1 week |
| Social interaction | Avoid interactions, except with parents | Hugging therapists; better eye contact, improved mood | 1 week |
| Bowel movements | Sometimes loose, pale stools | At first constipated for 2–3 days, then normal dark brown stools | 2–3 days |
| Movements | On toes, abnormal hand and arm positions; flexion of left arm; motor tics | A decrease in most abnormal movements but still has hyperactivity, especially in the hands | 1 week |

Case 3. D. T., a 4 year old boy, was referred for chronic diarrhea with foul smelling stools which were positive for blood. Autistic Disorder was diagnosed at ace 2-½. He had significant delays in speech and cognitive development with limited social skills. Because of his chronic diarrhea with foul smelling stools, he was referred to an allerologist, and multiple food allergies were diagnosed. He was placed on a significantly restricted diet, without any improve-ment in the consistency of his stools. He was also not potty-trained. He underwent an upper gastrointestinal endoscopy, and his pancreato-biliary response to secretin was excessive with an output of 8 ml/minute. Histological study revealed mild reflux esophagitis. The culture of his duodenal fluid for candida and bacteria was negative. His chronic diarrhea resolved. Most of the "claimed" antigenic foods were reintroduced into his diet without difficulty. The post-secretin behavioral evaluations were performed at three weeks and two months after the procedure. His language, social, and communication skills improved significantly (Table 6). A second infusion of secretion 3 months later accelerated his improvement in his language and communication skills.

TABLE 6

Changes after Secretin stimulation in case #3 (age 4 yrs)

| Category | Before | Changes |
|---|---|---|
| Alertness, concentration | Staring into space; self-stimulation (chewed hands, clothing, objects); does not pay attention | Chewing clothing, hands, and licking have stopped. Overall more alert. he is able to stay on tasks until completion. |
| Correct responses to drills/commands | Often guessing; not paying attention; 50% correct responses | Rarely guessing. Very tuned in. Perhaps 80% correct responses |
| Cognitive | Engaged in random, aimless activities (dumping toys, clicking all over the computer screen, turing it on and off) | Actions are more purposeful. Playing sequencing, matching, and memory games on the computer. Listening to and observing stories attentively. |
| Receptive language | Variable; understood 50% of commands; mostly one-step commands | Understands almost everything. Understands two-step commands. Understands and is able to respond to the question: How many? |
| Expressive language | Rarely repeats words; one word only, two words, no sentences | Repeating almost everything. Still no sentences, but has definite interest in finding out the names of things! He tries repeatedly to make his message clear. Recognizes and reads a number of letters of the alphabet. Knows and can say numbers up to 10. |
| Social interaction | Shy. Slow to warm up to people. At school engaged in a lot of parallel play | Now has a friend at school. He participates actively in group activities and plays more with his brother and sister. He helps with simple household chores when asked. He shares food with sister. |
| Eye contact | Limited eye contact with parents, siblings | More eye contact. Seeks out attention and once engaged in activity, shows good eye contact. |
| Sleep | Difficulty settling down at times. Would not allow bedtime storied to be read to completion. | Now goes to bed willing and happily. Takes great interest in his bedtime stories, but settles down right away when told to do so. |
| Fine motor skills | Poor. Unable to use knife, scissors, crayon, mouse. Seldom using spoon or fork. He used a spoon for eating porridge, but resisted using it for other foods. | Now uses fork and spoon much more readily and accurately. Uses mouse very precisely. Starting to hold crayon better and use scissors better. |
| Activity level. | Hyperactive even during drills; self simulations during drills and school. | Less hyperactive. More settled. More attentive and compliant to tasks. Will bounce in place on trampoline when needs to self regulate. |
| | When watching videos, for example, he would jump up and down and shriek with excitement. | When he watches videos, he imitates, and anticipates all actions, gestures and some words, clearly following and enjoying the story line. |
| Appetite | Was on highly restrictive diet for over a year. He ate well, but was frustrated by diet. | Normal diet seems to satisfy him more. No longer needs excessive quantities and actually |

TABLE 6-continued

Changes after Secretin stimulation in case #3 (age 4 yrs)

| Category | Before | Changes |
|---|---|---|
| | Seemed to require enormous quantities of food to satisfy his appetite. | leaves snacks, treats in favor of activities. He eats like a normal four year old. |
| Bowel movements | Loose stools or diarrhea | Normal bowel movement since week three |
| Movements | Jumping in response to videos, music | Now he sits down and enjoys listening to music, even hums along. |

Typical pancreatic juice output in children without behavioral abnormalities is approximately 1–2 ml/minute between the ages of 1 and 6, and the adult response varies between 1.6 to 5.9 ml/minute[56,57]. The average response rate in each of the three cases reported above was 107.5 and 8 ml/minute, respectively. Additionally, in each case, administration of secretin produced relief from autistic symptoms, and the second injection resulted in further improvement in their behavior and language functions.

Group Results

The number of children on whom we have collected data and/or completed analysis from specific tests varies and the N for each group is given in the graphs, tables or texts. For certain comparisons, the children were divided into two groups based on the presence or absence of chronic diarrhea.

Improved Stool Consistency

We evaluated seven children reported to have chronic loose stools. Interestingly, all of them had an improvement in the consistency of stools after the endoscopy and secretin injection. In five children this improvement was permanent; however, two had a relapse in their diarrhea later.

Prevalence of Reflux Esophagitis

We asked the parents specific questions regarding unexplained irritability or sudden aggressive behavior in their children. Six out of 15 children had these symptoms. Histological examination of 11 esophageal biopsy specimens provided confirming evidence of reflux esophagitis in 5 (45.5%). In addition, one child whose parents did not report this problem also had inflammation in the esophagus. This 45.5% incidence of esophagitis may suggest a common upper gastrointestinal motility problem in autistic children. The prevalence of reflux esophagitis in Western countries is estimated to be only 2%[58]. Children with esophagitis received at least two months treatment with prokinetic (Cisapride) and H2 blocker (Zantac) medications.

Digestive Enzyme anal Pancreatico-biliary Fluid Analyses

Figure 4:
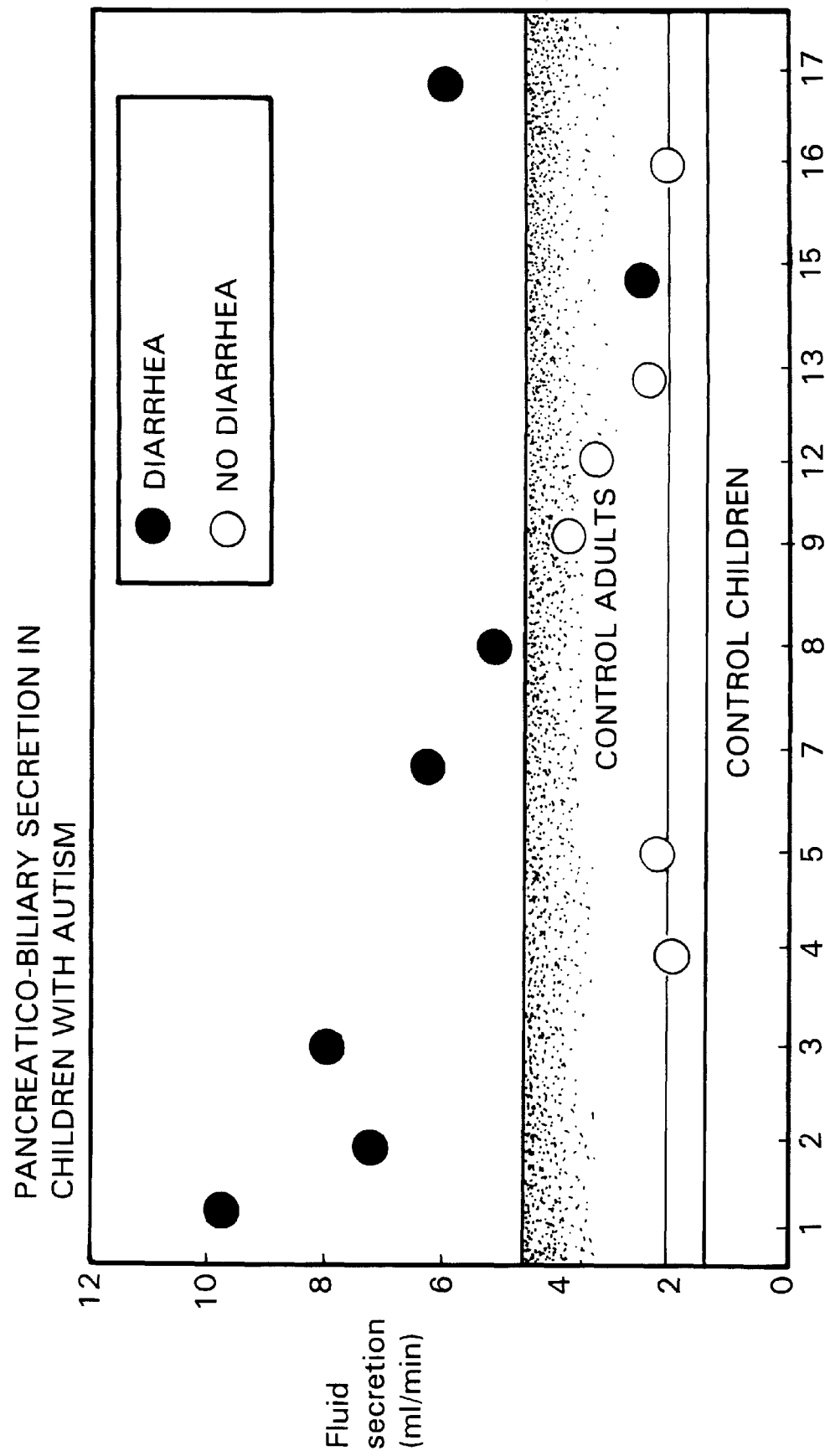
FIG. 4: Depicts pancreatico-biliary secretion of children with autism.

Rate of Pancreatico-biliary Secretion:

The time required to collect basal duodenal fluid samples (1–2 ml) prior to secretin administration was 2–5 minutes, which was similar to that of non-autistic controls. The average stimulatory response for secretin in children, 3–7 years of age, is 1–2 ml/min based on our data by using the same endoscopic collection technique. Published adult responses using duodenal intubation and extended periods of specimen collection vary between 1.5 and 4.9 ml/min[56,57]. Six out of 7 autistic patients who had chronic loose stools had pancreatico-biliary secretion rates above 5 ml/min (FIG. 4). It was observed that all children, after secretin injection, had an extensive pancreato-biliary secretory response when compared to non-autistic patients. The highest rate of secretion was 10ml/min in one child.

pH, Protein and Enzymes:

The pH of the collected fluid varied between pH 6 and 8.8. The protein content of basal samples was between 0.27 mg/ml and 2.46 mg/l and for samples collected immediately after secretin injection varied between 0.58 and 2.9 mg/ml. The protein content of final samples (due to the dilution effect) was between 0.62 and 1.79 mg/ml.

All of the duodenal fluid enzyme activities were within the normal range based on assays performed in our Laboratory on specimens from 215 children without pancreatic disease, i.e., cystic fibrosis.

Disaccharidases and Glucoamylase

The intestinal brush border membrane enzymes -disaccharidases and glucoamylase- were measured in 12 children. Four children each had one abnormal enzyme activity and in 1 boy the activities of two enzymes were low (Table 7). In summary, abnormal levels in at least one of the carbohydrate digestive enzymes was found in 5/12 children (41.6%). The most frequent abnormality was hypolactasia (abnormally low lactase level).

TABLE 7

Abnormal disaccharidase and glucoamylase enzyme activities in autistic children

| | Lactase | Maltase | Sucrase | Palatinase | Glucoamylase |
|---|---|---|---|---|---|
| Below 3d percentile | 3 | 1 | 0 | 1 | 1 |

Culture of tile Duodenal Fluid.

Four out of the 15 children who underwent endoscopic procedure had urine tests for organic acid and the results suggested that they have intestinal yeast overgrowth. Duodenal fluid specimens from 11 children were tested for both bacteria and fungi (Candida) and the tests for all the patients were normal, including those with positive urine organic acid tests.

Gastrointestinal Honnone and Serotonin Blood Levels

Blood Concentrations Prior to and After Secretin Injection

Figure 5:
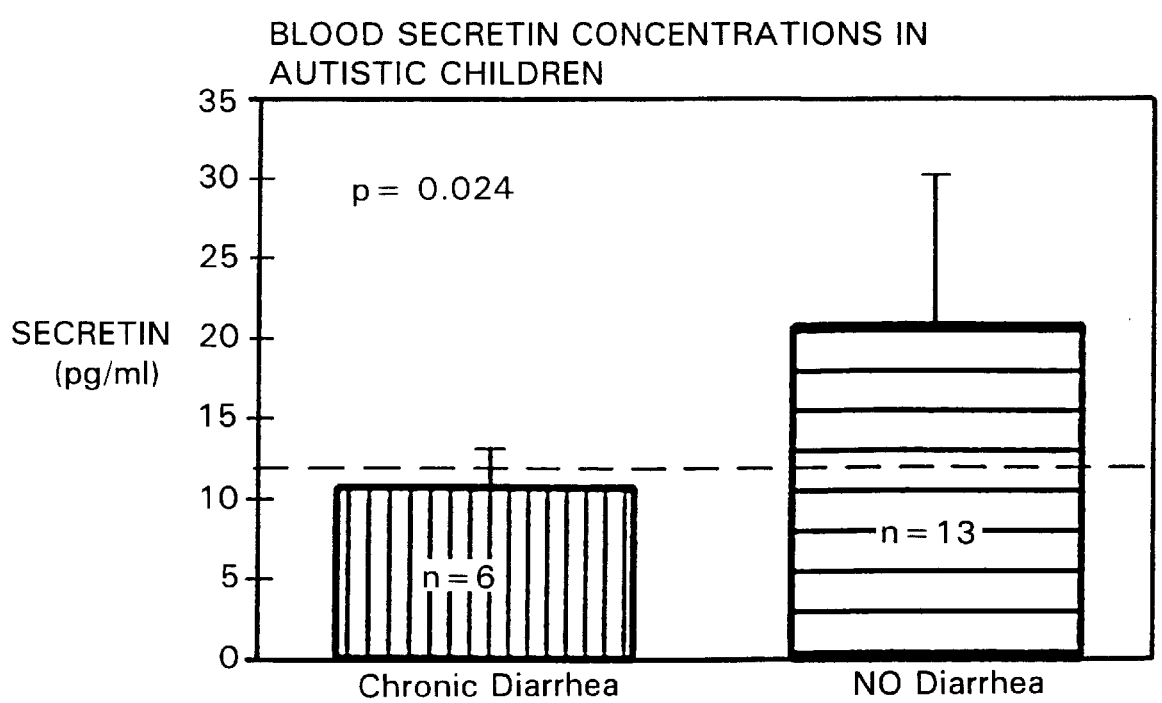
FIG. 5: Depicts blood secretin concentrations in autistic children.
Figure 6:
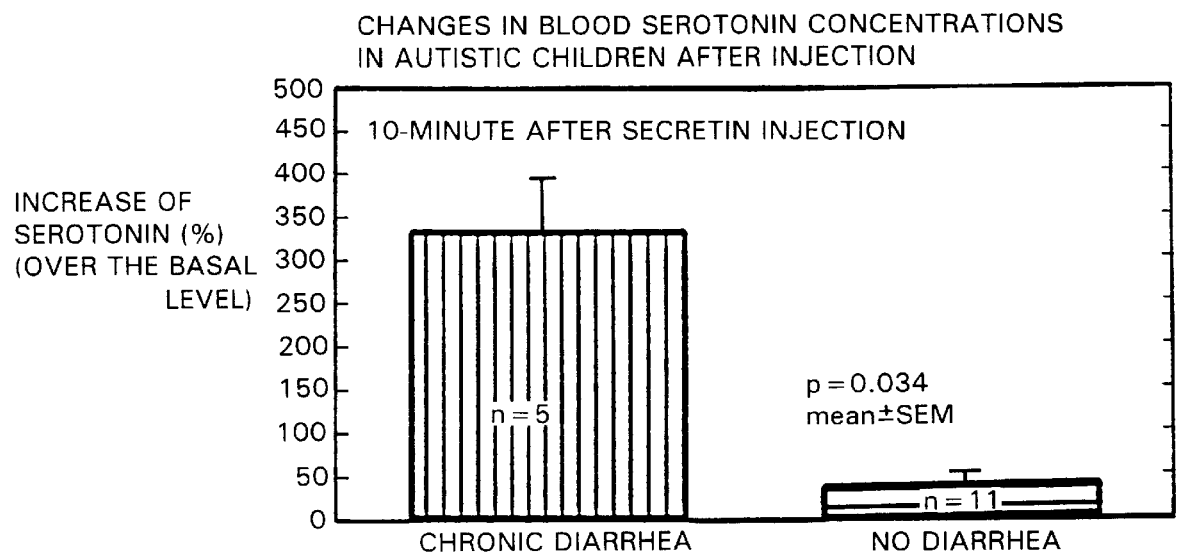
FIG. 6: Depicts changes in blood serotonin concentrations in autistic children after secretin injection.

The average basal secretin level in blood was significantly lower in children with chronic diarrhea (p<0.024) (FIG. 5). Interestingly, the basal serotonin level after 9–12 hours of fasting was normal in all patients (N=16), however, ten minutes after secretin injection, children with chronic diarrhea showed a significant elevation in their blood serotonin level (FIG. 6). We repeated this test in two children with the highest elevations and they showed the same degree of response in their blood serotonin level after secretin adninistration. Elevated serotonin levels have been reported in approximately 30% of patients with autism[59-65]. However, it is not clear from these papers whether the serotonin was measured after fasting or following meals. While there is no change in the blood serotonin levels in healthy adult volunteers after meals[66], our data showing that a certain fasting autistic children have increased serotonin levels after secretin injection may indicate that the serotonin levels should be measured in the fasting state in all autistic patients. It is possible that the reported increased blood serotonin levels were the consequence of a secretin release after meals. Our finding suggest that there may be two subgroups of patients with autistic behavior based on the serotonin response to secretin injection and possibly to meals as well. The relevance of this finding to the etiology of autism and to the familiar occurrence of hyperserotonemia in family members needs to be addressed in the future. There was no change at all and no subgroup differences in the blood levels of VIP, substance P or CCK after secretin injection. Peptide Y (measured in four children) showed no abnormality in blood levels either before or after the secretin administration.

Blood Secretin Concentrations after Duodenal Acidification

Figure 1B:
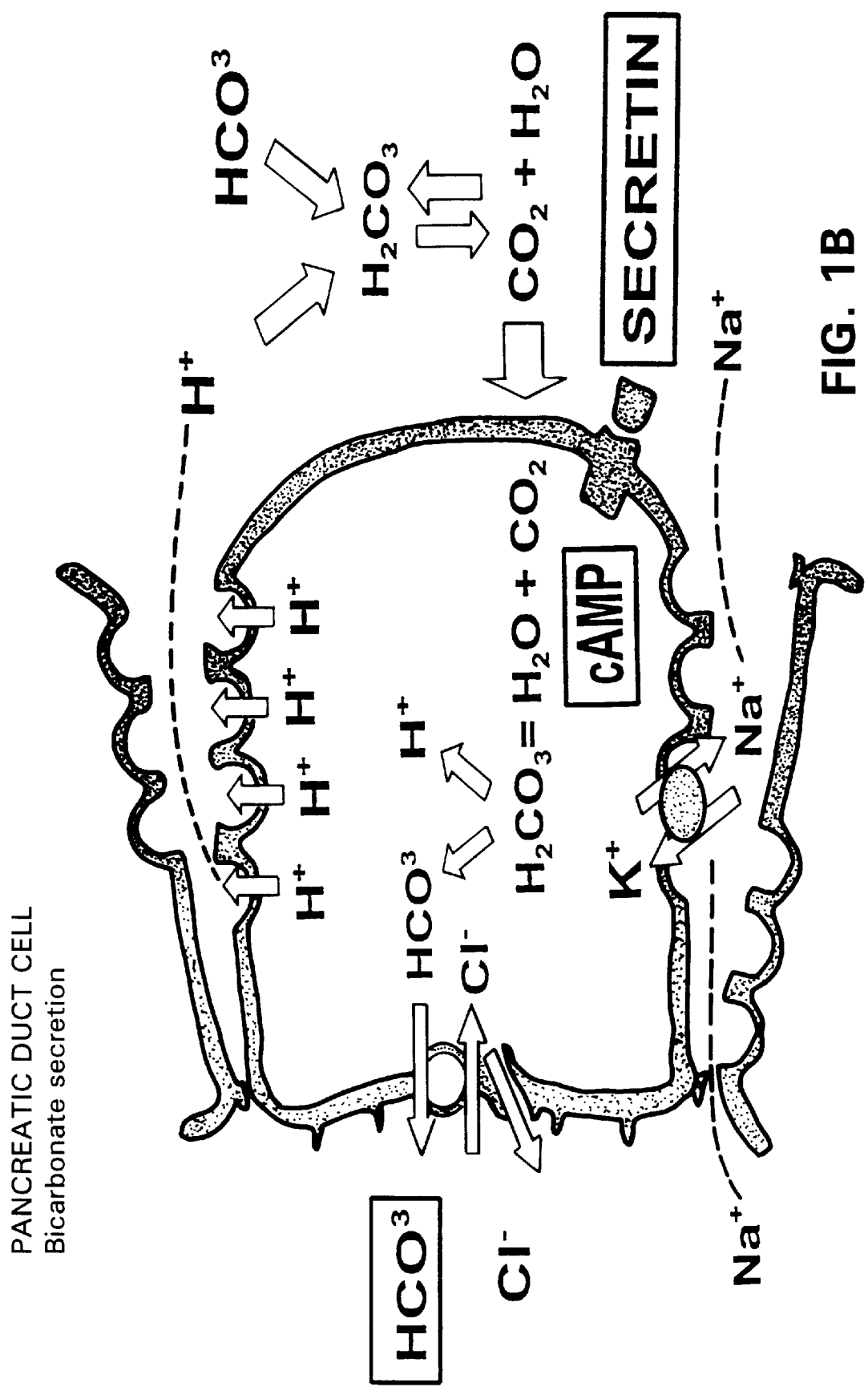
Figure 1C:
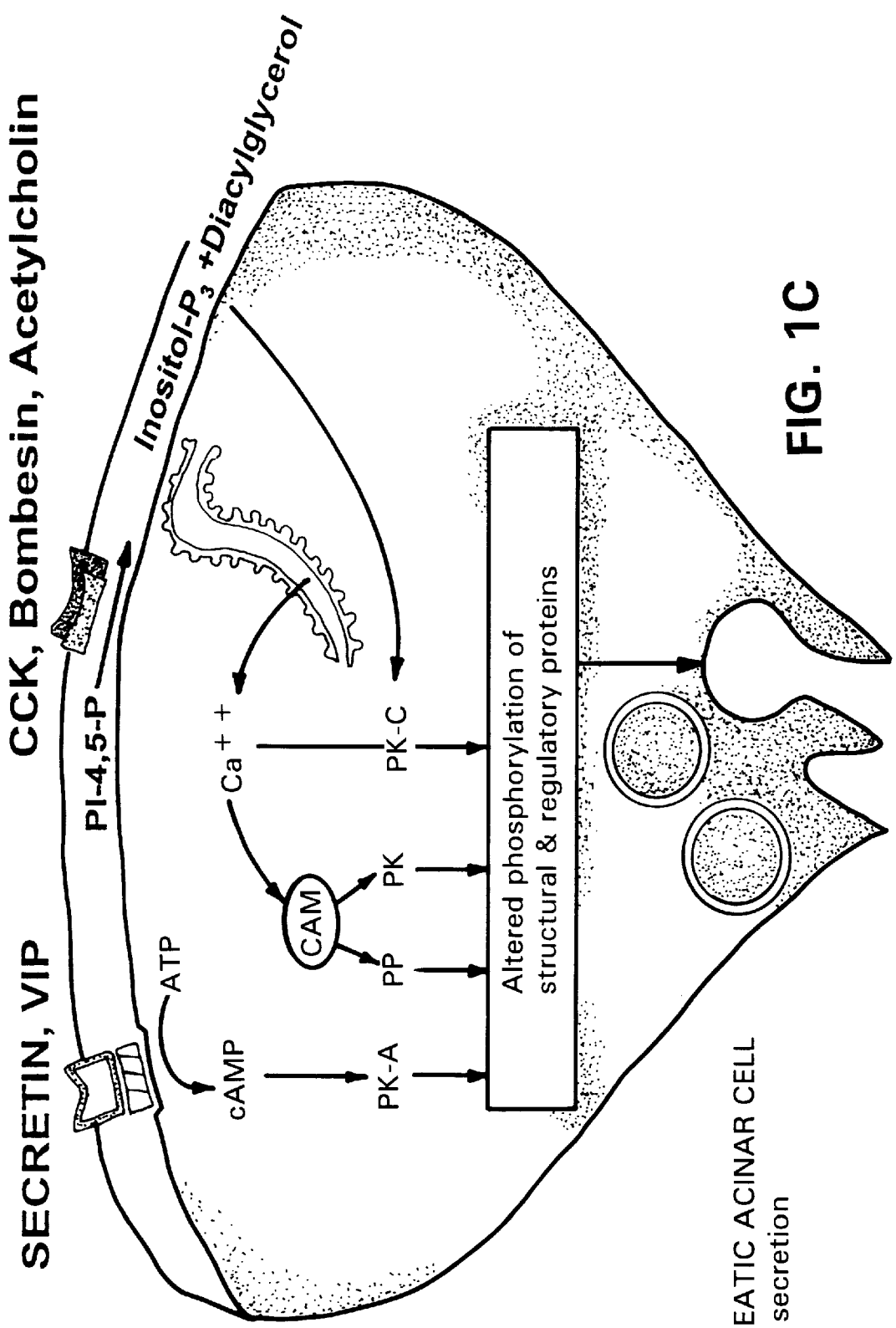
Figure 2:
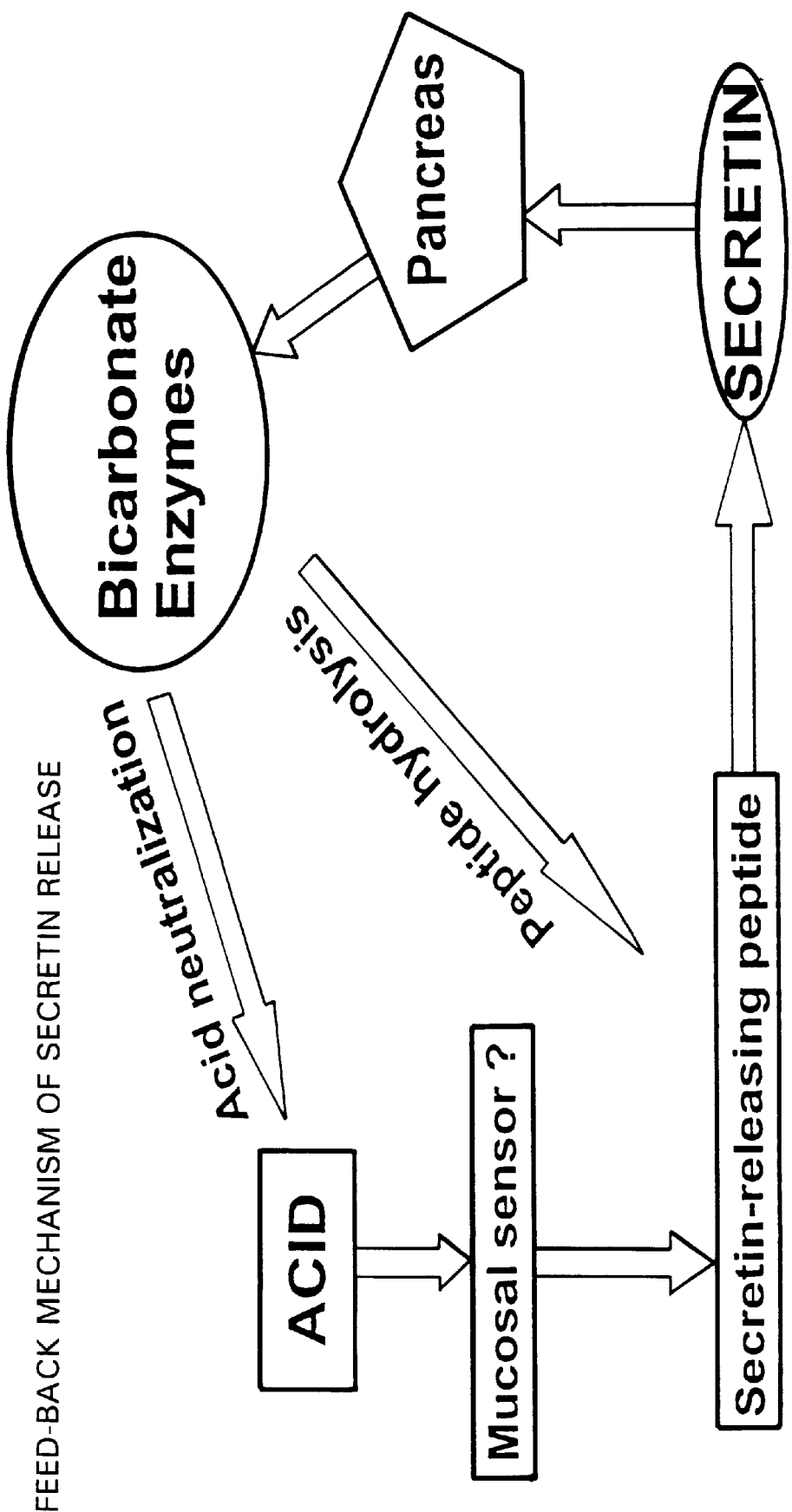
FIG. 2: Depicts the feed-back mechanism of secretin release.
Figure 7:
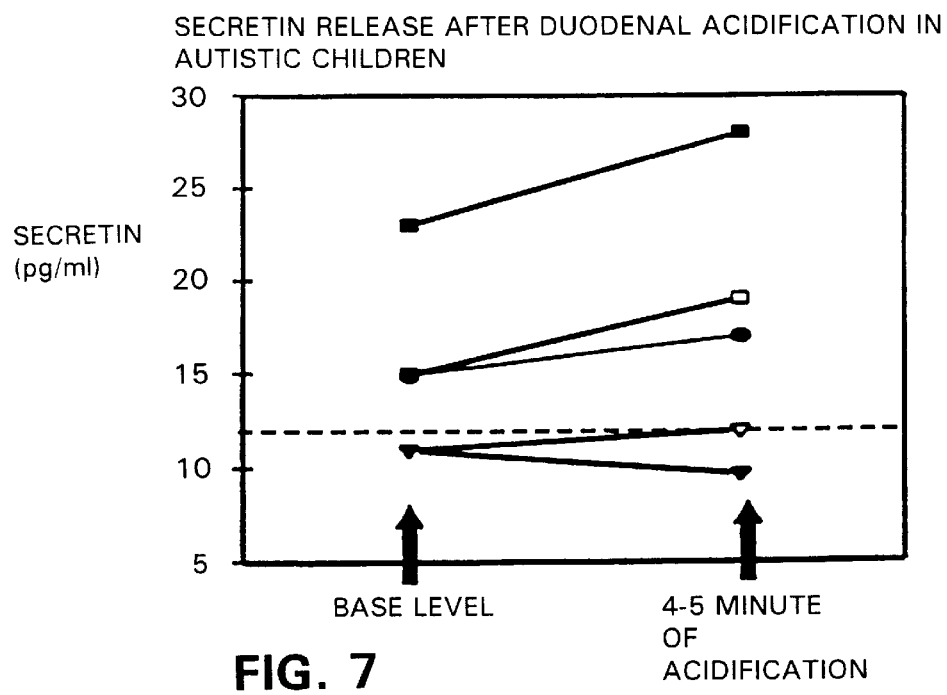
FIG. 7: Depicts secretin release after duodenal acidification in autistic children.

The normal physiologic process of secretin release from the intestinal S-(secretin) cells has been outlined earlier (FIGS. 1–2). We examined this response in 5 children during endoscopy by measuring secretin release following the acid washing of the duodenum. This acidification, which decreases pH to below 4.5, should release secretin into the blood. FIG. 7 shows the secretin levels in blood before and after 4–5 minutes of acidification. Although the sample number did not allow a clear conclusion it appears that children with low base secretin level less likely release secretin than children whose base level was in the normal range.

Based on our findings, we propose there are two subgroups of autistic patients distinguished on the basis of gastrointestinal symptoms, fasting blood secretin levels, and secretory responses to either duodenal acidification or secretin injection (Table 8).

TABLE 8

Subgroups of patients based on the secretin and serotonin measurements

|  | Group I. | Group II. |
| --- | --- | --- |
| Main gastrointestinal symptoms | Chronic loose stools/Diarrhea | No diarrhea |
| Basal secretin level | Low (<12 pg/ml) | Normal (>12 pg/ml) |
| Pancreatic secretion | Increased (>5 ml/min) | Normal (<4 ml/min) |
| Response to duodenal acidification | <2 pg/ml elevation of secretin | >2 pg/ml elevation of secretin |
| Serotonin level after secretin injection | >50% elevation | <50% elevation |

Behavior Evaluations

The number and type of evaluation techniques that were employed increased across subjects as did the degree of sophistication of the professional staff involved in the design and conduct of the evaluation approaches. Specifically, data on the first seven subjects consisted of brief clinical observations, parental report, analysis of videotapes, and reports of evaluations by professionals who had conducted routine assessments not specifically dictated by our research protocol. Whereas, data on the second eight subjects studied consisted of the same methods described above, as well as with the addition of direct observation of behavior employing a standard functional analysis of structured videotape samples (analyzed in random order by blind raters); standard assessments including Communication and Symbolic Behavior Scales (CSBS), Pre-School Language Scales—3 (PSLS), Bayley Scales of Infant Development: Second Edition, Vineland Adaptive Behavior Scales, Childhood Autism Rating Scale (CARS), and Behavior Observation System (BOS). Further, the evaluation team for the last eight subjects involved professionals from the areas of neuropsychology, behavioral psychology and developmental pediatrics from both the University of Maryland School of Medicine and the Kennedy Krieger Institute/Johns Hopkins University School of Medicine.

The findings on all fifteen subjects are truly exciting. For example, in terms of parental report and non-protocol dictated evaluations, dramatic changes in cognitive, social, language, and age appropriate skills were reported for four of the first seven subjects studied. For one child (JB) —a 3-year, 3-month-old boy presenting with chronic diarrhea and autistic symptoms, including no eye contact and no social interaction—significant changes occurred in both his gastrointestinal symptoms and behavior within three weeks after the procedure. Specifically, his chronic diarrhea resolved and he was able to be potty trained. Dramatic changes occurred in his autistic behavior in terms of a dramatic improvement in eye contact, alertness, expressive language and fine motor skills. Follow-up eight months after the procedure indicated that he had retained these improvements, especially with regard to cognitive skills. Most impressively, the latest formal evaluation indicates that his diagnosis has changed from a low functioning autistic child to a social, non-autistic, speech delayed child. A second case (AS)—an older boy (5-years, 9-months of age) with chronic diarrhea and autistic symptomatology first noticed at two years of age—demonstrated progressive improvement in cognitive skills over the five-week period following the administration of secretin. Similarly, the third case (DT)—a 4-year, 3-month-old boy with chronic diarrhea, evidence of blood in the stool, reports of allergies to seventeen food substances, autistic symptoms including severe aggression, no social interaction, and highly distractable attention—showed post-secretin changes including significant improvements in language, social, and communication skills. The last of the four cases (DP)—a 3-year, 10-month-old boy with chronic diarrhea, no speech, no eye contact, and a significant sleep disorder—improved after the secretin injection in that he was able to be potty trained within three weeks and showed significant improvement in language skills in general and expressive language gains in particular.

In terms of the last eight subjects studied, in addition to parental reports comparable to the first four successes, some of the standardized test scores for this last group of subjects indicated quite impressive gains. One child (WB)—a 3 year, 1 month-old boy with autistic symptomatology but without gastrointestinal symptoms, showed a 37% increase within four months on the CSBS scale as well as an increase in language skills equivalent to five months to one year in development as measured by the PSLS and lastly, an 11 point increase on the Bayley Scale of Development. The second child (SG)—3 years, 10 month-old boy, who presented with chronic diarrhea, but in terms of autistic symptomatology was one of the highest functioning children studied, showed evidence of impressive gains, including a 25% increase over a period in the CSBS, as well as six-to-nine month increases in language skills, and an increase in all five areas tested on the Vineland Scale of Adaptive Behaviors. A third subject (JP)—3 year, 9 month-old boy with chronic diarrhea presented with a variety of autistic symptomatology, including poor eye contact, no social interactions, self-stimulatory behavior, and delayed echolalia; but after the administration of secretin his markedly high activity level was decreased by 50% as measured by actometers and he showed an increase on the BOS of 22%. The last case described here showed both initial, small improvements and later quite dramatic changes post secretin administration; specifically, this case (BA)—3 years, 8 month-old boy with chronic loose stools presented with autistic symptoms of solitary play, echolalia, and poor social interaction; whereas immediately after secretin administration, a 22% increase in the scores on the Vineland Scale of Adaptive Behavior was noted as well as a delayed reaction reported by the parents some one-to-two months later that included improved eye contact, increased focus on tasks, as well as improvements in language.

In summary, more than half of the children who received secretin were found to have reductions in autistic symptoms and positive changes in cognitive, language, and social skills that were considerably greater than that which would be expected from developmental maturation. This novel relationship between pancreato-biliary secretion and autistic disorder enables a novel therapy for the treatment of the symptoms of autistic syndromes, comprising the administration of a therapeutically effective, preferably intravenous, dose of secretin to an individual suffering from autistic spectrum disorders. The relationship further enables a differential diagnosis for autistic syndrome, comprising an analysis of an individual's pancreatic response, or blood/intestinal biopsy specimen, for the presence of secretin and comparison of the levels to known norms.

We hereby incorporate by reference our article published in January 1998 in the *Journal of the Association for Academic Minority Physicians* entitled "Improved Social and Language Skills in Patients with Autistic Spectrum Disorders Following Secretin Administration." In addition, all references cited herein are incorporated by reference in their entirety.

1. *Diagnostic and Statistical Manual of Mental Disorders*, American Psychiatric Association. 1994; 4th edition.
2. Sugiyama T. Abe T, "The Prevalence of autism in Nagoya, Japan: a total population study", *Journal of Autism & Developmental Disorders*, 1989; 19(1):87–96.
3. Tanoue Y, Oda S, Asano F, Kawashima K, "Epidemiology of infantile autism in southern Ibaraki, Japan: differences in prevalence in birth cohorts", *Journal of Autism & Developmental Disorders*, 1988; 18(2): 155–66.
4. Lotspeich L J, Ciaranello R D, "The neurobiology and genetics of infantile autism" [Review], *International Review of Neurobiology*, 1993; 35:87–129.
5. Bauman M, Kemper T L, "Histoanatomic observations of the brain in early infantile autism", *Neurology*, 1985; 35(6):866–74.
6. Raymond G V, Bauman M L, Kemper T L, "Hippocampus in autism: a Golgi analysis", *Acta Neuroparhologica*, 1996; 91(1):117–9.
7. Minshew N, "In vivo brain chemistry of autism", Magnetic resonance spectroscopy studies in *The Neurobiology of Autism*, M. Bauman and T L. Kemper (editors), The Johns Hopkins Press, Baltimore, 1994, 1994:66–85.
8. Bauman M, Kemper T, "Neuroanatomic observations of the brain in autism" in *The Neurobiology of Autism*, M. Bauman and T L. Kemper (editors), The Johns Hopkins Press, Baltimore, 1994, 1994:119–45.
9. Hoon A H, Jr., Reiss A L, "The mesial-temporal lobe and autism: case report and review" [Review], *Developmental Medicine & Child Neurology*, 1992; 34(3):252–9.
10. Bachevalier J, Merjanian P. "The contribution of medial temporal lobe structures in infantile autism: a neurobehavioral study in primates", in *The Neurobiology of Autism*, M. Bauman and T L. Kemper (editors), The Johns Hopkins Press. Baltimore, 1994, 1994: 146–69.
11. Dawson G, Klinger L G, Panagiotides H, Lewy A, Castelloe P, "Subgroups of autistic children based on social behavior display distinct patterns of brain activity", *Journal of Abnormal Child Psychology*, 1995; 23(5):569–83.
12. George M S, Costa D C, Kouris K. Ring H A, Ell P J. "Cerebral blood flow abnormalities in adults with infantile autism", Journal of Nervous & Mental Disease, 1992; 180(7):413–7.
13. Olsson I. Steffenburg S. Gillber C. "Epilepsy in autism and autisticlike conditions: a population-based study", *Archives of Neurology*, 1988; 45(6):666–8.
14. Anderson G M, Freedman D X, Cohen D J, et al, "Whole blood serotonin in autistic and normal subjects", *Journal of Child Psychology & Psychiatry & Allied Disciplines*, 1987; 28(6): 885–900.
15. Garnier C, Comoy E, Barthelemy C. et al, "Dopamine-beta-hydroxylase (DBH) and homovanillic acid (HVA) in autistic children", *Journal of Autism & Developmental Disorders*, 1988; 16(1):23–9.
16. Bouvard M P, Leboyer M. Launay J M. et al. "Low-dose naltrexone effects on plasma chemistries and clinical symptoms in autism: a double-blind, placebo-controlled study", *Psychiatry Research*. 1995; 58(3):191–201.
17. Weizman A, Weizman R, Szekely G A, Wijsenbeek H, Livni E, "Abnormal immune response to brain tissue antigen in the syndrome of autism", American Journal of Psychiatry, 1982; 139 (11): 1462–5.
18. McDougle C. Price L, Volkmar F, "Recent advances in the pharmacotherapy of autism and related conditions", *Child and Adolescent Psychiatric Clinics of North America*. 1994; 3(1):71–89.
19. Campbell M. Overall J E, Small A M, et al, "Naltrexone in autistic children: an acute open dose range tolerance trial", *Journal of the American Academy of Child & Adolescent Psychiatry*, 1989; 28(2):200–6.
20. Willemsen-Swinkels S H, Buitelaar J K, Weijnen F G, vanEngeland H, "Placebo-controlled acute dosage naltrexone study in young autistic children", *Psychiatry Research*, 1995; 58(3):203–15.
21. Zioudrou C, Streaty R A, Klee W A. "Opioid peptides derived from food proteins: the exorphins", *Journal of Biological Chemistry*. 1979; 254(7):2446–9.
22. Fukodome A, Yoshikawa M. "Opioid peptides derived from wheat gluten: their isolation and characterization", *FEBS*, 1992; 296(1):107–11.
23. Reichelt K L, Hole K, Hamberger A, et al, "Biologically active peptide-containing fractions in schizophrenia and childhood autism" [Review], *Advances in Biochemical Psychopharmacology*, 1981; 28:627–43.
24. Knivsberg A-M, Wilg K, Lind G, Nodland M, Reichelt K L, "Dietary intervention in autistic syndromes", *Brain Dysfunct*, 1990; 3:315–27.
25. Warren R P, Yonk L J. Burger R A, et al, "Deficiency of suppressor-inducer (CD4+CD45RA+) T cells in autism", *Immunological Investigations*, 1990; 1(3):245–51.
26. D'Eufernia P, "Abnormal intestinal permeability in children with autism", *Acta Paediatrica*, 1996; 85:1076–9.
27. Inokuchi H. Fujimoto S, Hattori T. Kawai K, "Triated thymidine radioautographic study on the origin and renewal of secretin cells in the rat duodenum", *Gastroenterology*, 1985; 89(5): 1014–20.
28. Leiter A B. Chey W Y, Kopin A S. "Secretin" in *Gut peptides: Biochemistry and Physiology* edited by J H Walsh and G J Dockray, Raven Press, Ltd. New York. 1994:147–93.
29. Lenzen R, Alpini G. Tavoloni N. "Secretin stimulates bile ductular secretory activity through the cAMP system", *American Journal of Physiology*, 1992; 263(4 pt 1):G527–32.
30. Pollack P F. Wood J G, Solomon T, "Effect of secretin on growth of stomach, small intestine, and pancreas of developing rats", *Digestive Diseases & Sciences*, 1990; 35(6):749–58.
31. McGill J M, Basavappa S, Gettys T W, Fitz J G, "Secretin activates Cl-channels in bile duct epithelial cells through a cAMP-dependent mechanism", *American Journal of Physiology*, 1994; 266(4 pt 1):G731–6.
32. Lebenthal E, Clark B, "Immunoglobin concentrations in the duodenal fluids of infants and children II, The Effect 32. ...of pancreozymin and secretin", *American Journal of Gastroenterology*, 1981; 75(6):436–9.
33. Fara J W, Madden K S, "Effect of secretin and cholecystokinin on small intestinal blood flow distribution." *American Journal of Physiology*. 1975; 229(5):1365–70.
34. Lawrence J A. Bryant D, Roberts K B, Barrowman J A, "Effect of secretin on intestinal lymph flow and composition in the rat", *Quarterly Journal of Experimental Physiology*, 1981; 66(3):297–305.
35. Fukumoto Y, Okita K, Yasunaga M, et a., "A new therapeutic trial of secretin in the treatment of intrahepatic cholestasis", *Gastroenterologia Japonica*, 1989; 24(3):298–307.
36. Fukumoto Y, Okita K. Kodama T. et al, "Therapeutic effect of secretin in patients with jaundice; double-blind placebo-controlled multicentric trial", *Journal of Gastroenterology*, 1996; 31 (3):394–403.
37. Mutt V, Jorpes J E, Magnusson S, "Structure of porcine secretin: the amino acid sequence", European *Journal of Biochemistry*, 1970; 15(3):513–9.
38. Carlquist M, Jornvall H, Mutt V, "Isolation and amino acid sequence of bovine secretin", *FEBS Letters*, 1981; 127(1):71–4.
39. Fremeau R T, Jr., Korman L Y, Moody R T W, "Secretin stimulates cyclic AMP formation in the rat brain", *Journal of Neurochemistry*, 1986; 46(6):1947–55.
40. Kimura F, Mitsugi N, Arita J, Akema T, Yoshida K, "Effects of preoptic injections of gastrin, cholecystokinin, secretin, vasoactive intestinal peptide and P H I on the secretion of luteinizing hormone and prolactin in ovariectomized estrogen-primed rats", *Brain Research*, 1987; 410(2):315–22.
41. Charlton C G, T L O D, Miller R L, Jacobowitz D M, "Secretin immunoreactivity in rat and pig brain", *Peptides*, 1981; 2 suppl 1:45–9.
42. Charlton C G T L O D, Miller R L, Jacobowitz D M, "Secretin in the rat hypothalamo-pituitary system: localization, identification and characterization," *Peptides*, 1982; 3(3):565–7.
43. Itoh N, Furuya T, Ozaki K, Ohta M, Kawasaki T, "The secretin precursor gene: structure of the coding region and expression in the brain", *Journal of Biological Chemistry*, 1991; 266(19): 12595–8.
44. Fremeau R T, Jr., Jensen R T, Charlton C G, Miller R L, T L O D, Moody T W, "Secretin: specific binding to rat brain membranes", *Jounial of Neuroscience*, 1983; 3(8): 162–05.
45. Patel DR, Kong Y. Sreedharan S P, "Molecular cloning and expression of a human secretin receptor", *Molecular Pharmacology*, 1995; 47(3):467–73.
46. vanCalker D, Muller M. Hamprecht B, "Regulation by secretin, vasoactive intestinal peptide, and somatostatin of cyclic AMP accumulation in cultured brain cells", *Proceedings of the National Academy of Sciences of the United States of America*. 1980: 77(11):6907–11.
47. Karelson E, Laasik J, Sillard R. "Regulation of adenylate cyclase by galanin, neuropeptide Y, secretin and vasoactive intestinal polypeptide in rat frontal cortex, hippocampus and hypothalamus". *Neuropeptides*, 1995; 28(1):21–8.
48. Redgate E S, Deupree J D, Axelrod J. "Interaction of neuropeptides and biogenic amines on cyclic adenosine monophosphate accumulation in hypothalamic nuclei", *Brain Research*, 1986; 365 (1): 61–9.
49. DeLong G R, "Autism, amnesia, hippocampus, and learning", [Review] *Neuroscience & Biobehavioral Reviews*, 1992: 16(1):63–70.
50. Usdin T B, Bonner T I, Mezey E. "Two receptors for vasoactive intestinal polypeptide with similar specificity and complementary distributions", *Endocrinology*, 1994; 135(6):2662–80.
51. Schwarzschild M A, Zigmond R E, "Secretin and vasoactive intestinal peptide activate tyrosine hydroxylase in sympathetic nerve endings", *Journal of Neuroscience*, 1989; 9(1):160–06.
52. Charlton C G, Miller R L. Crawley J N, Handelmann G E, T L O D,"Secretin modulation of behavioral and physiological functions in the rat", Peptides, 1983; 4(5):739–42.
53. Sparrow S S, Balla D A, Cicchetti E V, Vineland Adaptive Behavior Scales: Interview Edition, American Guidance Service, Circle Pines. Minnesota, 1984.
54. Achenbach T M, *Manual for the Child Behavior Checklist/4–18* and 1991 *Profile*, Burlington V T, University of Vermont Department of Psychiatry, 1981.
55. Schopler E, Reichler R J, DeVellis R F, Daly K, "Toward objective classification of childhood autism: Childhood Autism Rating Scale (CARS)", *Journal of Autism and Developmental Disorders*, 1980; 19:91–103.
56. Dreiling D A, Hillander F, "Studies in pancreatic function II: a statistical study of pancreatic secretion following secretin in patients without pancreatic disease", *Gastroenterology* 1950; 15: 620.
57. Howat H T, Braganza J M, "Assessment of pancreatic dysfunction in man" in The exocrine pancreas, Howat HT, Salres H, Eds., W B Saunders, Philadelphia. 1979:129.
58. Wienbeck, M, Barnert J. Epidemiology of reflux disease and reflux esophagitis. Scan *J Gastroenterol*1989;156 (Suppl):7–13.
59. Cook E H, Jr. Leventhal B L. Heller W, Metz J, Wainwright M, Freedman DX. Autistic children and their first-degree relatives: relationships between serotonin and norepinephrine levels and intelligence. Journal of *Neuropsychiatry & Clinical Neuroscience* 1990;2(3):268–74.
60. Cook E H. Autism: review of neurochemical investigation. Synapse 1990;6(3):292–308.
61. Cook E H, Leventhal B L. The serotonin system in autism. *Current Opinion in Pediatrics* 1996;8(4):348–54.
62. Cook E H. Jr., Arora R C, Anderson G M. Berry-Kravis E M, Yan S Y, Yeoh H C, et al. Platelet serotonin studies in hyperserotonemic relatives of children with autistic disorder. *Life Sciences* 1993;52(25):2005–15.
63. Bursztejn C. Ferrari P, Dreux C. Braconnier A, Lancrenon S. Metabolism of serotonin in autism in children. *Encephale* 1988,14(6):413–9.
64. Singh V K, Singh E A. Warren R P. Hyperserotoninemia and scrotonin receptor antibodies in children with autism but not mental retardation. *Biological Psychiatry* 1997;41 (6):753–5.
65. Abramson R K. Wright H H. Carpenter R. Brennan W, Lumpuy 0 Cole E. et al. Elevated blood serotonin in autistic probands and their first-degree relatives. *Journal of Autism & Developmental Disorders*1989: 19(3):397–407.
66. Anderson G M. Feibel F C, Wetlaufer L A. Schlicht K R, Ort S M. Cohen D J. Effect of a meal on human whole blood serotonin. *Gastroenterology* 1985;88(1 Pt 1):86–9.

While a specific embodiment of the invention has been shown and described in detail to illustrate the application of the principles of the invention, it will be understood that the invention may be embodied otherwise without departing from such principles, and that various modifications, alternate constructions, and equivalents will occur to those skilled in the art given the benefit of this disclosure. Various changes and modifications can be made therein without departing from the spirit and scope of the invention. Thus, the invention is not limited to the specific embodiment described herein, but is defined by the appended claims.

What is claimed:

1. A method for treating a gastrointestinal dysfunction in an individual exhibiting one or more symptoms of an autistic disorder, the method comprising administering to the individual an effective amount of secretin, wherein the gastrointestinal dysfunction is improved.

2. The method of claim 1 wherein the secretion of pancreatico-biliary fluid is stimulated by administering to the individual an effective amount of secretin.

3. The method of claim 1, wherein the gastrointestinal dysfunction is chronic loose stools.

4. The method of claim 1, wherein the gastrointestinal dysfunction is chronic diarrhea.

5. The method of claim 1, wherein the effective amount of secretin comprises about 2 IU of secretin per kg of the individual's body weight.

6. The method of claim 1, wherein the secretin is administered by intravenous, oral, intramuscular, intra-articular, intradermal, subcutaneous, inhalation, or rectal administration.

7. The method of claim 1, wherein the secretin is chosen from the group consisting of human secretin, porcine secretin, and bovine secretin.

8. The method of claim 1, wherein the secretin is synthetic secretin, natural secretin, or recombinant secretin.

9. The method of claim 1, wherein the secretin is administered as a single bolus.

10. The method of claim 1, wherein the secretin is administered at least once every three month.

11. The method of claim 1, wherein the secretin is administered at least once every three months.

12. A method for treating an individual exhibiting one or more symptoms of an-autistic disorder, the method comprising administering to the individual an amount of secretin sufficient to stimulate the endogenous release of serotonin in the individual, wherein one or more symptoms of autistic disorder are improved.

13. The method of claim 12, wherein the secretin is administered by intravenous, oral, intramuscular, intra-articular, intradermal, subcutaneous, inhalation, or rectal administration.

14. The method of claim 12, wherein the secretin is chosen from the group consisting of human secretin, porcine secretin, and bovine secretin.

15. The method of claim 12, wherein the secretin is synthetic secretin, natural secretin, or recombinant secretin.

16. The method of claim 12, wherein the secretin is administered as a single bolus.

17. The method of claim 12, wherein the secretin is administered at least once every month.

18. The method of claim 12, wherein the secretin is administered at least once every three months.

19. The method of claim 12, wherein the symptom is a qualitative impairment in social interaction as manifested by (a) impairment in the use of eye-to-eye gaze, facial expression, body posture, or gestures; (b) a failure to develop peer relationships appropiate to develomental level of the individual; (c) a lack of spontaneous sharing of enjoyment, interest, or achievements with other people; or (d) a lack of social or emotional reciprocity.

20. The method of claim 12, wherein the symptom is impairment in the use of eye-to-eye gaze, facial expression, body posture, or gestures.

21. The method of claim 12, wherein the symptom is a failure to develop peer relationships appropriate to developmental level of the individual.

22. The method of claim 12, wherein the symptom is a lack of spontaneous sharing of enjoyment, interests, or achievements with other people.

23. The method of claim 12, wherein the symptom is a lack of social or emotional reciprocity.

24. The method of claim 12, wherein the symptom is a qualitative impairment in communication as manifested by (a) a delay in or lack of spoken language; (b) in individuals with adequate speech, a marked impairment in the ability to initiate or sustain a conversation with others; (c) a stereotyped and repetitive use of language or idiosyncratic language; or (d) a lack of spontaneous make-believe or social imitative play appropriate to developmental level of the individual.

25. The method of claim 12, wherein the symptom is a delay in or lack of spoken language.

26. The method of claim 12, wherein the symptom is, in individuals with adequate speech, a marked impairment in the ability to initiate or sustain a conversation with others.

27. The method of claim 12, wherein the symptom is a stereotyped and repetitive use of language or idiosyncratic language.

28. The method of claim 12, wherein the symptom is a lack of spontaneous make-believe or social imitative play appropriate to developmental level of the individual.

29. The method of claim 12, wherein the symptom is a restricted, repetitive, and stereotyped pattern of behavior, interest, or activity, as manifested by (a) a preoccupation with one or more stereotyped and restricted patterns of interest that is abnormal in intensity or focus; (b) an apparently inflexible adherence to specific, nonfunctional routines or rituals; (c) a stereotyped and repetitive motor mannerism; or (d) a persistent preoccupation with parts of objects.

30. The method of claim 12, wherein the symptom is a preoccupation with one or more stereotyped and restricted patterns of interest that is abnormal in intensity or focus.

31. The method of claim 12, wherein the symptom is an apparently inflexible adherence to specific, nonfunctional routines or rituals.

32. The method of claim 12, wherein the symptom is a stereotyped and repetitive motor mannerism.

33. The method of claim 12, wherein the symptom is a persistent preoccupation with parts of objects.

34. The method of claim 12, wherein the symptom is a difficulty in falling asleep or repeated waking during sleep.

35. The method of claim 12, wherein the symptom is an impairment in alertness or concentration as manifested by staring into space or failure to pay attention to other people.

36. The method of claim 12, wherein the symptom is an impairment in receptive language as manifested by a lack of understanding.

37. The method of claim 12, wherein the symptom is an impairment in cognitive skills as manifested by random or aimless activities, or a lack of purposeful actions.

38. The method of claim 12, wherein the symptom is chronic loose stools.

39. The method of claim 12, wherein the symptom is chronic diarrhea.

40. A method for diagnosing an autistic disorder in an individual, the method comprising obtaining a sample of blood from the individual; and analyzing the blood level of secretin in the blood; wherein a decreased blood level of secretin compared to a normal secretin blood level indicates the possibility of autistic disorder in the individual.

41. The method of claim 40, wherein the normal secretin blood level is at least 12 pg/ml.

* * * * *